US011289183B2

(12) United States Patent
Kohlbrecher

(10) Patent No.: US 11,289,183 B2
(45) Date of Patent: *Mar. 29, 2022

(54) MATCHING DELAYED INFUSION AUTO-PROGRAMS WITH MANUALLY ENTERED INFUSION PROGRAMS

(71) Applicant: ICU Medical, Inc., San Clemente, CA (US)

(72) Inventor: Christopher E. Kohlbrecher, Poway, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/017,460

(22) Filed: Sep. 10, 2020

(65) Prior Publication Data

US 2021/0098106 A1    Apr. 1, 2021

Related U.S. Application Data

(63) Continuation of application No. 16/296,806, filed on Mar. 8, 2019, now Pat. No. 10,799,632, which is a
(Continued)

(51) Int. Cl.
*G16H 20/17*    (2018.01)
*A61M 5/142*    (2006.01)
(Continued)

(52) U.S. Cl.
CPC ............ *G16H 20/17* (2018.01); *A61M 5/142* (2013.01); *A61M 5/172* (2013.01); *G16H 40/67* (2018.01);
(Continued)

(58) Field of Classification Search
CPC ....... G16H 20/17; G16H 40/67; A61M 5/142; A61M 5/172; A61M 2005/14208;
(Continued)

(56) References Cited

U.S. PATENT DOCUMENTS 4,024,864 A    5/1977    Davies et al.
4,055,175 A    10/1977   Clemens et al.
(Continued)

FOREIGN PATENT DOCUMENTS

CA    2 060 151    8/1997
CA    2 125 300    10/1999
(Continued)

OTHER PUBLICATIONS

Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.
(Continued)

*Primary Examiner* — Ronald D Hartman, Jr.
(74) *Attorney, Agent, or Firm* — Knobbe, Martens, Olson & Bear, LLP

(57) ABSTRACT

A system and method that identifies delayed infusion programs at an infusion pump or with a first computer and an infusion pump. The first computer receives an infusion auto-program from a remote source, transmits the infusion auto-program to the infusion pump, and sends a stale auto-program to the infusion pump. The infusion pump receives a manual infusion program, saves and executes the manual infusion program, and compares the stale auto-program to the manual infusion program to identify potential matches between the stale auto-program and the manual infusion program. The infusion pump evaluates the potential matches and determines if the potential matches are within a predefined tolerance, continues to execute the at least one manual infusion program on the infusion pump if the potential matches are within the predefined tolerance, and remotely saves differences in the manual infusion program
(Continued)

and the at stale auto-program in a remote server for later analysis.

20 Claims, 7 Drawing Sheets

Related U.S. Application Data continuation of application No. 15/511,193, filed as application No. PCT/US2015/050128 on Sep. 15, 2015, now Pat. No. 10,238,799, which is a continuation of application No. 14/853,198, filed on Sep. 14, 2015, now Pat. No. 9,539,383.

(60) Provisional application No. 62/050,536, filed on Sep. 15, 2014.

(51) Int. Cl.
  *G16H 40/67* (2018.01)
  *A61M 5/172* (2006.01)
(52) U.S. Cl.
  CPC .......... *A61M 2005/14208* (2013.01); *A61M 2205/18* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/6054* (2013.01); *A61M 2205/6072* (2013.01)
(58) Field of Classification Search
  CPC ...... A61M 2205/18; A61M 2205/3561; A61M 2205/3584; A61M 2205/3592; A61M 2205/50; A61M 2205/502; A61M 2205/52; A61M 2205/6054; A61M 2205/6072
  See application file for complete search history.

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |

(56) References Cited

U.S. PATENT DOCUMENTS

| | | | |
|---|---|---|---|
| 5,447,164 A | 9/1995 | Shaya et al. | |
| 5,455,851 A | 10/1995 | Chaco et al. | |
| 5,461,365 A | 10/1995 | Schlager et al. | |
| 5,464,392 A | 11/1995 | Epstein et al. | |
| 5,465,082 A | 11/1995 | Chaco | |
| 5,485,408 A | 1/1996 | Blomquist | |
| 5,486,286 A | 1/1996 | Peterson et al. | |
| 5,493,430 A | 2/1996 | Lu et al. | |
| 5,496,273 A | 3/1996 | Pastrone et al. | |
| 5,505,828 A | 4/1996 | Wong et al. | |
| 5,507,288 A | 4/1996 | Bocker et al. | |
| 5,507,786 A | 4/1996 | Morgan et al. | |
| 5,508,499 A | 4/1996 | Ferrario | |
| 5,515,713 A | 5/1996 | Saugues et al. | |
| 5,520,637 A | 5/1996 | Pager et al. | |
| 5,522,798 A | 6/1996 | Johnson et al. | |
| 5,547,470 A | 8/1996 | Johnson et al. | |
| 5,554,013 A | 9/1996 | Owens et al. | |
| 5,562,615 A | 10/1996 | Nassif | |
| 5,577,169 A | 11/1996 | Prezioso | |
| 5,582,323 A | 12/1996 | Kurtenbach | |
| 5,582,593 A | 12/1996 | Hultman | |
| 5,594,786 A | 1/1997 | Chaco et al. | |
| 5,598,519 A | 1/1997 | Narayanan | |
| 5,620,608 A | 4/1997 | Rosa et al. | |
| 5,630,710 A | 5/1997 | Tune et al. | |
| 5,636,044 A | 6/1997 | Yuan et al. | |
| 5,643,212 A | 7/1997 | Coutre et al. | |
| 5,651,775 A | 7/1997 | Walker et al. | |
| 5,658,131 A | 8/1997 | Aoki et al. | |
| 5,658,250 A | 8/1997 | Blomquist et al. | |
| 5,665,065 A | 9/1997 | Colman et al. | |
| 5,669,877 A | 9/1997 | Blomquist | |
| 5,672,154 A | 9/1997 | Sillén et al. | |
| 5,681,285 A | 10/1997 | Ford et al. | |
| 5,685,844 A | 11/1997 | Marttila | |
| 5,687,717 A | 11/1997 | Halpern et al. | |
| 5,689,229 A | 11/1997 | Chaco et al. | |
| 5,697,899 A | 12/1997 | Hillman et al. | |
| 5,699,509 A | 12/1997 | Gary et al. | |
| 5,713,350 A * | 2/1998 | Yokota | G16H 20/10 600/300 |
| 5,713,856 A | 2/1998 | Eggers et al. | |
| 5,718,562 A | 2/1998 | Lawless et al. | |
| 5,719,761 A | 2/1998 | Gatti et al. | |
| 5,733,259 A | 3/1998 | Valcke et al. | |
| 5,738,102 A | 4/1998 | Lemelson | |
| 5,744,027 A | 4/1998 | Connell et al. | |
| 5,752,621 A | 5/1998 | Passamante | |
| 5,754,111 A | 5/1998 | Garcia | |
| 5,764,034 A | 6/1998 | Bowman et al. | |
| 5,764,159 A | 6/1998 | Neftel et al. | |
| 5,772,635 A | 6/1998 | Dastur et al. | |
| 5,774,865 A | 6/1998 | Glynn | |
| 5,778,256 A | 7/1998 | Darbee | |
| 5,778,345 A | 7/1998 | McCartney | |
| 5,781,442 A | 7/1998 | Engleson et al. | |
| 5,782,805 A | 7/1998 | Meinzer et al. | |
| 5,788,669 A | 8/1998 | Peterson | |
| 5,797,515 A | 8/1998 | Liff et al. | |
| 5,800,387 A | 9/1998 | Duffy et al. | |
| 5,814,015 A | 9/1998 | Gargano et al. | |
| 5,822,544 A | 10/1998 | Chaco et al. | |
| 5,822,715 A | 10/1998 | Worthington et al. | |
| 5,827,179 A | 10/1998 | Lichter et al. | |
| 5,832,448 A | 11/1998 | Brown | |
| 5,836,910 A | 11/1998 | Duffy et al. | |
| 5,850,344 A | 12/1998 | Conkright | |
| 5,867,821 A | 2/1999 | Ballantyne et al. | |
| 5,870,733 A | 2/1999 | Bass et al. | |
| 5,871,465 A | 2/1999 | Vasko | |
| 5,873,731 A | 2/1999 | Predergast | |
| 5,885,245 A | 3/1999 | Lynch et al. | |
| 5,897,493 A | 4/1999 | Brown | |
| 5,897,498 A | 4/1999 | Canfield, II et al. | |
| 5,910,252 A | 6/1999 | Truitt et al. | |
| 5,912,818 A | 6/1999 | McGrady et al. | |
| 5,915,240 A | 6/1999 | Karpf | |
| 5,920,054 A | 7/1999 | Uber, III | |
| 5,920,263 A | 7/1999 | Huttenhoff et al. | |
| 5,924,074 A | 7/1999 | Evans | |
| 5,931,764 A | 8/1999 | Freeman et al. | |
| 5,935,099 A | 8/1999 | Peterson et al. | |
| 5,935,106 A | 8/1999 | Olsen | |
| 5,941,846 A | 8/1999 | Duffy et al. | |
| 5,956,501 A | 9/1999 | Brown | |
| 5,957,885 A | 9/1999 | Bollish et al. | |
| 5,960,085 A | 9/1999 | de la Huerga | |
| 5,961,448 A | 10/1999 | Swenson et al. | |
| 5,967,559 A | 10/1999 | Abramowitz | |
| 5,971,594 A | 10/1999 | Sahai et al. | |
| 5,975,081 A | 11/1999 | Hood et al. | |
| 5,990,838 A | 11/1999 | Burns et al. | |
| 5,997,476 A | 12/1999 | Brown | |
| 6,000,828 A | 12/1999 | Leet | |
| 6,003,006 A | 12/1999 | Colella et al. | |
| 6,012,034 A | 1/2000 | Hamparian et al. | |
| 6,017,318 A | 1/2000 | Gauthier et al. | |
| 6,021,392 A | 2/2000 | Lester et al. | |
| 6,024,539 A | 2/2000 | Blomquist | |
| 6,024,699 A * | 2/2000 | Surwit | G16H 40/63 600/300 |
| 6,032,155 A | 2/2000 | de la Huerga | |
| 6,032,676 A | 3/2000 | Moore | |
| 6,039,251 A | 3/2000 | Holowko et al. | |
| 6,070,761 A | 6/2000 | Bloom et al. | |
| 6,073,106 A | 6/2000 | Rozen et al. | |
| 6,104,295 A | 8/2000 | Gaisser et al. | |
| 6,112,182 A | 8/2000 | Akers et al. | |
| 6,112,323 A | 8/2000 | Meizlik et al. | |
| RE36,871 E | 9/2000 | Epstein et al. | |
| 6,115,390 A | 9/2000 | Chuah | |
| 6,122,536 A | 9/2000 | Sun et al. | |
| 6,126,637 A | 10/2000 | Kriesel et al. | |
| 6,135,949 A | 10/2000 | Russo et al. | |
| 6,150,942 A | 11/2000 | O'Brien | |
| 6,151,643 A | 11/2000 | Cheng et al. | |
| 6,157,914 A | 12/2000 | Seto et al. | |
| 6,159,147 A | 12/2000 | Lichter et al. | |
| 6,167,567 A | 12/2000 | Chiles et al. | |
| 6,182,667 B1 | 2/2001 | Hanks et al. | |
| 6,189,105 B1 | 2/2001 | Lopes | |
| 6,195,589 B1 | 2/2001 | Ketcham | |
| 6,208,974 B1 | 3/2001 | Campbell et al. | |
| 6,222,323 B1 | 4/2001 | Yamashita et al. | |
| 6,223,440 B1 | 5/2001 | Rashman | |
| 6,226,277 B1 | 5/2001 | Chuah | |
| 6,227,371 B1 | 5/2001 | Song | |
| 6,234,176 B1 | 5/2001 | Domae et al. | |
| 6,241,704 B1 | 6/2001 | Peterson et al. | |
| 6,248,067 B1 | 6/2001 | Causey, III et al. | |
| 6,249,705 B1 | 6/2001 | Snell | |
| 6,257,265 B1 | 7/2001 | Brunner et al. | |
| 6,259,355 B1 | 7/2001 | Chaco et al. | |
| 6,269,340 B1 | 7/2001 | Ford et al. | |
| 6,270,455 B1 | 8/2001 | Brown | |
| 6,271,813 B1 | 8/2001 | Palalau | |
| 6,277,072 B1 | 8/2001 | Bardy | |
| 6,280,380 B1 | 8/2001 | Bardy | |
| 6,283,761 B1 | 9/2001 | Joao | |
| 6,285,665 B1 | 9/2001 | Chuah | |
| 6,292,860 B1 | 9/2001 | Cochcroft, Jr. | |
| 6,312,378 B1 | 11/2001 | Bardy | |
| 6,327,254 B1 | 12/2001 | Chuah | |
| 6,330,008 B1 | 12/2001 | Razdow et al. | |
| 6,339,718 B1 | 1/2002 | Zatezalo et al. | |
| 6,346,886 B1 | 2/2002 | de la Huerga | |
| 6,363,282 B1 | 3/2002 | Nichols et al. | |
| 6,371,719 B1 | 4/2002 | Hildebrandt | |
| 6,377,548 B1 | 4/2002 | Chuah | |
| 6,388,951 B1 | 5/2002 | Matsumoto et al. | |
| 6,406,426 B1 | 6/2002 | Reuss et al. | |
| 6,408,330 B1 | 6/2002 | de la Huerga | |
| 6,418,334 B1 | 7/2002 | Unger et al. | |

(56) References Cited

U.S. PATENT DOCUMENTS

| | | |
|---|---|---|
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Crnkovich et al. |
| 6,780,156 B2 | 8/2004 | Haueter et al. |
| 6,790,198 B1 | 9/2004 | White et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wermeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 | 1/2007 | Chung |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |

(56) References Cited

U.S. PATENT DOCUMENTS

| | | |
|---|---|---|
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |
| 7,420,472 B2 | 9/2008 | Tran |
| 7,432,807 B2 | 10/2008 | Schmitt |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,095,692 B2 | 1/2012 | Mehta et al. |
| 8,147,448 B2 | 4/2012 | Sundar et al. |
| 8,149,131 B2 | 4/2012 | Blomquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,312,272 B1 | 11/2012 | Serenyl et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 | 3/2013 | Leibner-Druska |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,480,648 B2 | 7/2013 | Burnett et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |

(56) References Cited

U.S. PATENT DOCUMENTS

| | | | |
|---|---|---|---|
| 8,922,330 B2 | 12/2014 | Moberg et al. | |
| 8,936,565 B2 | 1/2015 | Chawla | |
| 8,945,043 B2 | 2/2015 | Lee et al. | |
| 8,952,794 B2 | 2/2015 | Blomquist et al. | |
| 8,998,100 B2 | 4/2015 | Halbert et al. | |
| 9,026,370 B2 | 5/2015 | Rubalcaba et al. | |
| 9,069,887 B2 | 6/2015 | Gupta et al. | |
| 9,077,544 B2 | 7/2015 | Baker et al. | |
| 9,089,642 B2 | 7/2015 | Murphy et al. | |
| 9,114,217 B2 | 8/2015 | Sur et al. | |
| 9,123,077 B2 | 9/2015 | Silkaitis et al. | |
| 9,192,712 B2 | 11/2015 | DeBelser et al. | |
| 9,240,002 B2 | 1/2016 | Hume et al. | |
| 9,381,296 B2 | 7/2016 | Arrizza et al. | |
| 9,393,362 B2 | 7/2016 | Cozmi et al. | |
| 9,483,615 B2 | 11/2016 | Roberts | |
| 9,498,583 B2 | 11/2016 | Sur et al. | |
| 9,539,383 B2* | 1/2017 | Kohlbrecher | A61M 5/142 |
| 9,572,923 B2 | 2/2017 | Howard et al. | |
| 9,594,875 B2 | 3/2017 | Arrizza et al. | |
| 9,604,000 B2 | 3/2017 | Wehba et al. | |
| 9,641,432 B2 | 5/2017 | Jha et al. | |
| 9,649,431 B2 | 5/2017 | Gray et al. | |
| 9,662,436 B2 | 5/2017 | Belkin et al. | |
| 9,690,909 B2 | 6/2017 | Stewart et al. | |
| 9,707,341 B2 | 7/2017 | Dumas, III et al. | |
| 9,717,845 B2 | 8/2017 | Istoc | |
| 9,724,470 B2 | 8/2017 | Day et al. | |
| 9,764,082 B2 | 9/2017 | Day et al. | |
| 9,886,550 B2 | 2/2018 | Lee et al. | |
| 9,943,269 B2 | 4/2018 | Muhsin et al. | |
| 9,971,871 B2 | 5/2018 | Arrizza et al. | |
| 9,995,611 B2 | 6/2018 | Ruchti et al. | |
| 10,022,498 B2 | 7/2018 | Ruchti et al. | |
| 10,042,986 B2 | 8/2018 | Ruchti et al. | |
| 10,046,112 B2 | 8/2018 | Oruklu et al. | |
| 10,166,328 B2 | 1/2019 | Oruklu et al. | |
| 10,173,008 B2 | 1/2019 | Simpson et al. | |
| 10,238,799 B2 | 3/2019 | Kohlbrecher | |
| 10,238,801 B2 | 3/2019 | Wehba et al. | |
| 10,242,060 B2 | 3/2019 | Butler et al. | |
| 10,300,194 B2 | 5/2019 | Day et al. | |
| 10,311,972 B2 | 6/2019 | Kohlbrecher et al. | |
| 10,314,974 B2 | 6/2019 | Day et al. | |
| 10,333,843 B2 | 6/2019 | Jha et al. | |
| 10,430,761 B2 | 10/2019 | Hume et al. | |
| 10,434,246 B2 | 10/2019 | Silkaitis et al. | |
| 10,463,788 B2 | 11/2019 | Day | |
| 10,617,815 B2 | 4/2020 | Day et al. | |
| 10,646,651 B2 | 5/2020 | Day et al. | |
| 10,692,595 B2 | 6/2020 | Xavier et al. | |
| 10,741,280 B2 | 8/2020 | Xavier et al. | |
| 10,757,219 B2 | 8/2020 | Moskal | |
| 10,765,799 B2 | 9/2020 | Belkin et al. | |
| 10,799,632 B2* | 10/2020 | Kohlbrecher | G16H 40/67 |
| 10,812,380 B2 | 10/2020 | Jha et al. | |
| 10,861,592 B2 | 12/2020 | Xavier et al. | |
| 10,898,641 B2 | 1/2021 | Day et al. | |
| 10,950,339 B2 | 3/2021 | Xavier et al. | |
| 10,964,428 B2 | 3/2021 | Xavier et al. | |
| 11,013,861 B2 | 5/2021 | Wehba et al. | |
| 11,037,668 B2 | 6/2021 | Ruchti et al. | |
| 11,052,193 B2 | 7/2021 | Day et al. | |
| 11,139,058 B2 | 10/2021 | Xavier et al. | |
| 2001/0016056 A1 | 8/2001 | Westphal et al. | |
| 2001/0031944 A1 | 10/2001 | Peterson et al. | |
| 2001/0032099 A1 | 10/2001 | Joao | |
| 2001/0037060 A1 | 11/2001 | Thompson et al. | |
| 2001/0044731 A1 | 11/2001 | Coffman et al. | |
| 2001/0048027 A1 | 12/2001 | Walsh | |
| 2001/0051787 A1 | 12/2001 | Haller et al. | |
| 2001/0056358 A1 | 12/2001 | Dulong et al. | |
| 2002/0010595 A1 | 1/2002 | Kapp | |
| 2002/0013551 A1 | 1/2002 | Zaitsu et al. | |
| 2002/0013723 A1 | 1/2002 | Mise | |
| 2002/0015018 A1 | 2/2002 | Shimazu et al. | |
| 2002/0016568 A1 | 2/2002 | Lebel et al. | |
| 2002/0019584 A1 | 2/2002 | Schulze et al. | |
| 2002/0021700 A1 | 2/2002 | Hata et al. | |
| 2002/0026103 A1 | 2/2002 | Norris et al. | |
| 2002/0029776 A1 | 3/2002 | Blomquist | |
| 2002/0032583 A1 | 3/2002 | Joao | |
| 2002/0040208 A1 | 4/2002 | Flaherty et al. | |
| 2002/0040282 A1 | 4/2002 | Bailey et al. | |
| 2002/0044043 A1 | 4/2002 | Chaco et al. | |
| 2002/0082728 A1 | 6/2002 | Mueller et al. | |
| 2002/0087115 A1 | 7/2002 | Hartlaub | |
| 2002/0087116 A1 | 7/2002 | Hartlaub | |
| 2002/0095486 A1 | 7/2002 | Bahl | |
| 2002/0103675 A1 | 8/2002 | Vanelli | |
| 2002/0123905 A1 | 9/2002 | Goodroe et al. | |
| 2002/0143580 A1 | 10/2002 | Bristol et al. | |
| 2002/0152239 A1 | 10/2002 | Bautista-Lloyd et al. | |
| 2002/0154600 A1 | 10/2002 | Ido et al. | |
| 2002/0173702 A1 | 11/2002 | Lebel et al. | |
| 2002/0173875 A1 | 11/2002 | Wallace et al. | |
| 2002/0194329 A1 | 12/2002 | Alling | |
| 2003/0009244 A1 | 1/2003 | Engleson | |
| 2003/0013959 A1 | 1/2003 | Grunwald et al. | |
| 2003/0014222 A1 | 1/2003 | Klass et al. | |
| 2003/0014817 A1 | 1/2003 | Gallant et al. | |
| 2003/0025602 A1 | 2/2003 | Medema et al. | |
| 2003/0028082 A1 | 2/2003 | Thompson | |
| 2003/0036683 A1 | 2/2003 | Kehr et al. | |
| 2003/0036744 A1 | 2/2003 | Struys et al. | |
| 2003/0047126 A1 | 3/2003 | Tomaschko | |
| 2003/0050621 A1 | 3/2003 | Lebel et al. | |
| 2003/0059750 A1 | 3/2003 | Bindler et al. | |
| 2003/0060688 A1 | 3/2003 | Ciarniello et al. | |
| 2003/0069963 A1 | 4/2003 | Jayant et al. | |
| 2003/0079746 A1 | 5/2003 | Hickle | |
| 2003/0097529 A1 | 5/2003 | Arimilli et al. | |
| 2003/0104982 A1 | 6/2003 | Wittmann et al. | |
| 2003/0105389 A1 | 6/2003 | Noonan et al. | |
| 2003/0106553 A1 | 6/2003 | Vanderveen | |
| 2003/0115358 A1 | 6/2003 | Yun | |
| 2003/0120384 A1 | 6/2003 | Haitin et al. | |
| 2003/0125662 A1 | 7/2003 | Bui | |
| 2003/0130616 A1 | 7/2003 | Steil | |
| 2003/0135087 A1 | 7/2003 | Hickle et al. | |
| 2003/0139701 A1 | 7/2003 | White et al. | |
| 2003/0140928 A1 | 7/2003 | Bui et al. | |
| 2003/0140929 A1 | 7/2003 | Wilkes et al. | |
| 2003/0141981 A1 | 7/2003 | Bui et al. | |
| 2003/0143746 A1 | 7/2003 | Sage, Jr. | |
| 2003/0144878 A1 | 7/2003 | Wilkes et al. | |
| 2003/0158749 A1 | 8/2003 | Olchanski et al. | |
| 2003/0187338 A1 | 10/2003 | Say et al. | |
| 2003/0200116 A1 | 10/2003 | Forrester | |
| 2003/0204416 A1 | 10/2003 | Acharya | |
| 2003/0204781 A1 | 10/2003 | Peebles et al. | |
| 2003/0212364 A1 | 11/2003 | Mann et al. | |
| 2003/0212379 A1 | 11/2003 | Bylund et al. | |
| 2003/0212821 A1 | 11/2003 | Gillies et al. | |
| 2003/0217962 A1 | 11/2003 | Childers et al. | |
| 2004/0008123 A1 | 1/2004 | Carrender et al. | |
| 2004/0015132 A1 | 1/2004 | Brown | |
| 2004/0019607 A1 | 1/2004 | Moubayed et al. | |
| 2004/0030323 A1 | 2/2004 | Ullestad et al. | |
| 2004/0039257 A1 | 2/2004 | Hickle | |
| 2004/0057226 A1 | 3/2004 | Berthou et al. | |
| 2004/0064341 A1 | 4/2004 | Langan et al. | |
| 2004/0064342 A1 | 4/2004 | Browne et al. | |
| 2004/0064435 A1 | 4/2004 | Moubayed et al. | |
| 2004/0073811 A1 | 4/2004 | Sanin | |
| 2004/0077934 A1 | 4/2004 | Massad | |
| 2004/0078231 A1 | 4/2004 | Wilkes et al. | |
| 2004/0078236 A1 | 4/2004 | Stoodley et al. | |
| 2004/0085186 A1 | 5/2004 | Eveland et al. | |
| 2004/0104271 A1 | 6/2004 | Martucci et al. | |
| 2004/0122530 A1 | 6/2004 | Hansen | |
| 2004/0128162 A1 | 7/2004 | Schlotterbeck et al. | |
| 2004/0128163 A1 | 7/2004 | Goodman et al. | |
| 2004/0133441 A1 | 7/2004 | Brady et al. | |

(56) References Cited

U.S. PATENT DOCUMENTS

| | | |
|---|---|---|
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | McLaughlin |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |

(56) References Cited

U.S. PATENT DOCUMENTS

| | | |
|---|---|---|
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0233521 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0126969 A1 | 5/2008 | Blomquist |
| 2008/0139907 A1 | 6/2008 | Rao et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0200870 A1 | 8/2008 | Palmroos et al. |
| 2008/0214919 A1 | 9/2008 | Harmon et al. |
| 2008/0243055 A1 | 10/2008 | Fathallah et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0292645 A1 | 11/2010 | Hungerford et al. |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0138185 A1 | 6/2011 | Ju et al. |
| 2011/0175728 A1 | 7/2011 | Baker, Jr. |
| 2011/0178462 A1 | 7/2011 | Moberg et al. |
| 2011/0196748 A1 | 8/2011 | Caron et al. |
| 2011/0231216 A1 | 9/2011 | Fyke et al. |
| 2011/0257496 A1 | 10/2011 | Terashima et al. |

(56) References Cited

U.S. PATENT DOCUMENTS

| | | |
|---|---|---|
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016295 A1 | 1/2012 | Tsoukalis |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0066501 A1 | 3/2012 | Xiong |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0130308 A1 | 5/2012 | Silkaitis et al. |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0035633 A1 | 2/2013 | Chawla |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0085689 A1 | 4/2013 | Sur et al. |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0138452 A1 | 5/2013 | Cork et al. |
| 2013/0144206 A1 | 6/2013 | Lee et al. |
| 2013/0150824 A1 | 6/2013 | Estes et al. |
| 2013/0158504 A1 | 6/2013 | Ruchti et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0261993 A1 | 10/2013 | Ruchti et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0039446 A1 | 2/2014 | Day |
| 2014/0058350 A1 | 2/2014 | Stewart et al. |
| 2014/0163517 A1 | 6/2014 | Finan et al. |
| 2014/0180711 A1 | 6/2014 | Kamen et al. |
| 2014/0194817 A1 | 7/2014 | Lee et al. |
| 2014/0221959 A1 | 8/2014 | Gray et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0288947 A1 | 9/2014 | Simpson et al. |
| 2014/0297329 A1 | 10/2014 | Rock |
| 2014/0350513 A1 | 11/2014 | Oruklu et al. |
| 2014/0358077 A1 | 12/2014 | Oruklu et al. |
| 2014/0366878 A1 | 12/2014 | Baron |
| 2015/0001285 A1 | 1/2015 | Halbert et al. |
| 2015/0005935 A1 | 1/2015 | Bae et al. |
| 2015/0058044 A1 | 2/2015 | Butler et al. |
| 2015/0066531 A1 | 3/2015 | Jacobson et al. |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0134265 A1 | 5/2015 | Kohlbrecher et al. |
| 2015/0141955 A1 | 5/2015 | Ruchti et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0230760 A1 | 8/2015 | Schneider |
| 2015/0328396 A1 | 11/2015 | Adams et al. |
| 2015/0371004 A1 | 12/2015 | Jones |
| 2015/0379237 A1 | 12/2015 | Mills et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0051749 A1 | 2/2016 | Istoc |
| 2016/0051751 A1 | 2/2016 | Silkaitis et al. |
| 2016/0103960 A1 | 4/2016 | Hume et al. |
| 2016/0228633 A1 | 8/2016 | Welsch et al. |
| 2016/0241391 A1 | 8/2016 | Fenster |
| 2016/0285876 A1 | 9/2016 | Perez et al. |
| 2016/0350513 A1 | 12/2016 | Jacobson et al. |
| 2017/0024534 A1 | 1/2017 | Arrizza et al. |
| 2017/0147761 A1 | 5/2017 | Moskal et al. |
| 2017/0246388 A1 | 8/2017 | Kohlbrecher |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0331735 A1 | 11/2017 | Jha et al. |
| 2018/0008772 A1 | 1/2018 | Wehba et al. |
| 2018/0028742 A1 | 2/2018 | Day et al. |
| 2018/0043094 A1 | 2/2018 | Day et al. |
| 2018/0121613 A1 | 5/2018 | Connely, IV et al. |
| 2018/0126067 A1 | 5/2018 | Ledford et al. |
| 2018/0181712 A1 | 6/2018 | Ensey et al. |
| 2018/0247712 A1 | 8/2018 | Muhsin et al. |
| 2018/0322948 A1 | 11/2018 | Drost et al. |
| 2019/0006044 A1 | 1/2019 | Brask |
| 2019/0096518 A1 | 3/2019 | Pace |
| 2019/0132196 A1 | 5/2019 | Trivedi et al. |
| 2019/0147998 A1 | 5/2019 | Ruchti et al. |
| 2019/0228863 A1 | 7/2019 | Dharwad et al. |
| 2019/0229982 A1 | 7/2019 | Ikuta et al. |
| 2019/0240405 A1 | 8/2019 | Wehba et al. |
| 2019/0243829 A1 | 8/2019 | Butler et al. |
| 2019/0245942 A1 | 8/2019 | Moskal |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0027541 A1 | 1/2020 | Xavier et al. |
| 2020/0027542 A1 | 1/2020 | Xavier et al. |
| 2020/0027543 A1 | 1/2020 | Xavier et al. |
| 2020/0027548 A1 | 1/2020 | Xavier et al. |
| 2020/0027549 A1 | 1/2020 | Xavier et al. |
| 2020/0027550 A1 | 1/2020 | Xavier et al. |
| 2020/0027551 A1 | 1/2020 | Xavier et al. |
| 2020/0028837 A1 | 1/2020 | Xavier et al. |

(56) References Cited

U.S. PATENT DOCUMENTS

| | | | |
|---|---|---|---|
| 2020/0028914 A1 | 1/2020 | Xavier et al. |
| 2020/0035355 A1 | 1/2020 | Xavier et al. |
| 2020/0054825 A1 | 2/2020 | Kamen et al. |
| 2020/0061291 A1 | 2/2020 | Day et al. |
| 2020/0206413 A1 | 7/2020 | Silkaitis et al. |
| 2020/0282139 A1 | 9/2020 | Susi |
| 2020/0306443 A1 | 10/2020 | Day |
| 2020/0330685 A1 | 10/2020 | Day |
| 2020/0335194 A1 | 10/2020 | Jacobson et al. |
| 2020/0353167 A1 | 11/2020 | Vivek et al. |
| 2020/0353168 A1 | 11/2020 | Keenan et al. |
| 2021/0043296 A1 | 2/2021 | Xavier et al. |
| 2021/0045640 A1 | 2/2021 | Poltorak |
| 2021/0050097 A1 | 2/2021 | Xavier et al. |
| 2021/0085855 A1 | 3/2021 | Belkin et al. |
| 2021/0098107 A1 | 4/2021 | Xavier et al. |
| 2021/0105206 A1 | 4/2021 | Jha et al. |
| 2021/0252210 A1 | 8/2021 | Day et al. |

FOREIGN PATENT DOCUMENTS

| | | |
|---|---|---|
| CA | 2 898 825 | 7/2014 |
| CO | 01110843 | 8/2003 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/057729 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/124569 | 8/2015 |

(56) References Cited

FOREIGN PATENT DOCUMENTS

| WO | WO 2017/176928 | 10/2017 |
|---|---|---|
| WO | WO 2019/219290 | 11/2019 |
| WO | WO 2020/227403 | 11/2020 |

OTHER PUBLICATIONS

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.
Beard et al., "Total Quality Pain Management: History, Background, Resources", Abbott Laboratories, TQPM Survey History, available Feb. 2015 or earlier, pp. 1-3.
Bektas et al., "Bluetooth Communication Employing Antenna Diversity", Proceedings of Eight IEEE International Symposium on Computers and Communication, Jul. 2003, pp. 6.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Braun, "Infusomat® Space and Accessories", Instructions for Use, Nov. 2010, pp. 68. http://corp.bbraun.ee/Extranet/Infusionipumbad/Kasutusjuhendid/Vanad/Kasutusjuhend-Infusomat_Space(vers688J,inglise_k).pdf.
Brownlee, Seth, "Product Spotlight: The Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf.
"CareAware® Infusion Management", Cerner Store, as printed May 12, 2011, pp. 3, https://store.cerner.eom/items/7.
Chen et al., "Enabling Location-Based Services on Wireless LANs", The 11th IEEE International Conference on Networks, ICON 2003, Sep. 28-Oct. 1, 2003, pp. 567-572.
"Computer Dictionary", Microsoft Press, Third Edition, Microsoft Press, 1997, pp. 430 & 506.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
East PhD et al., "Digital Electronic Communication Between ICU Ventilators and Computers and Printers", Respiratory Care, Sep. 1992, vol. 37, No. 9, pp. 1113-1122.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Felleiter et al., "Data Processing in Prehospital Emergency Medicine", International journal of Clinical Monitoring and Computing, Feb. 1995, vol. 12, No. 1, pp. 37-41.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gabel et al., "Camp: A Common API for Measuring Performance", 21st Large Installations System Administration Conference (LISA '07), 2007, pp. 49-61.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D. et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", http://www.trackingsystem.com/forbusinesses/corporate-trackingsystem/1098-gps-tracker-formedicalequipment.html, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Numbers from 3000 to 59,999", Technical Service Manual, Graseby Medical Ltd., Apr. 2002, Issue A, pp. 71.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.

(56) References Cited

OTHER PUBLICATIONS

Hospira, GemStar® Pain Management Infusion System 9-084-PR1-2-2, www.hospira.com/products/gemstar_painmanagement.aspx, Jan. 28, 2010, pp. 1-2.
Introducing Abbott TQPM (Total Quality Pain Management), Abbott Laboratories, Abbott Park, IL, May 2000, pp. 1-4.
"Infusion Pump", Wikipedia.org, as last modified Mar. 27, 2014, in 3 pages, https://web.archive.org/web/20140703024932/https://en.wikipedia.org/wiki/Infusion_pump.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety in Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.
Metnitz et al., "Computer Assisted Data Analysis in Intensive Care: the ICDEV Project—Development of a Scientific Database System for Intensive Care", International Journal of Clinical Monitoring and Computing, Aug. 1995, vol. 12, No. 3, pp. 147-159.
Micrel Medical Devices, "MP Daily +" http://web.archive.org/web/20130803235715/http://www.micrelmed.com/index.aspx?productid=9 as archived Aug. 3, 2013 in 1 page.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", http://www.omnilink.com/portablemedicalequipmenttracking/, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Philips, "IntelliSpace Event Management and IntelliVue Patient Monitoring", Release 10, 2011, http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2, pp. 2.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", Oct. 2009, pp. 72. http://static.medonecapital.com/manuals/userManuals/Sigma-Spectrum-Operator-Manual-October-2009.pdf.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

(56) References Cited

OTHER PUBLICATIONS

Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpj4209-832.pdf.
Slack, W.V., "Information Technologies for Transforming Health Care", https://www.andrew.cmu.edu/course/90-853/medis.dir/otadocs.dir/03ch2.pdf, Ch. 2, 1995, pp. 29-78.
Smith, Joe, "Infusion Pump Informatics", CatalyzeCare: Transforming Healthcare, as printed May 12, 2011, pp. 2.
Sodders, Lisa, "VA Center Keeps Medicine in Right Hands", The Capital-Journal, Dec. 4, 1999, pp. 1-2.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.

Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
International Search Report and Written Opinion received in PCT Application No. PCT/US2015/050128, dated Jan. 4, 2016 in 11 pages.
International Preliminary Report on Patentability and Written Opinion received in PCT Application No. PCT/US2015/050128, dated Mar. 30, 2017 in 10 pages.
"Context-Free Grammar", Wikipedia.org, as last modified Mar. 5, 2010 in 11 pages, https://en.wikipedia.org/w/index.php/?title=Context-free_grammar&oldid=347915989.
"Download", Free On-Line Dictionary of Computing, as archived Jun. 16, 2010 in 1 page, http://web.archive.org/web/20100616010314/https://foldoc.org/download.
Edworthy, Judy, "Medical Audible Alarms: A Review", Journal of the American Medical Informatics Association, vol. 20, No. 3, 2013, pp. 584-589.
"File Verification", Wikipedia.org, as last modified Oct. 11, 2011 in 2 pages, https://en.wikipedia.org/w/index.php?title=File_verification&oldid=455048290.
"McKesson Automation and ALARIS Medical Systems Developing Point-of-Care Bar Coding Solution to Improve IV Medication Safety", PR Newswire, NY, Dec. 9, 2002, pp. 4.
"Software Versioning", Wikipedia.org, dated Oct. 16, 2011 in 11 pages, https://en.wikipedia.org/w/index.php?title=Software_versioning&oldid=455859110.
Ahn et al., To"wards Scalable Authentication in Health Services", Eleventh IEEE International Workshops on Enabling Technologies: Infrastructure for Collaborative Enterprises, Jun. 2002, pp. 83-88.

\* cited by examiner

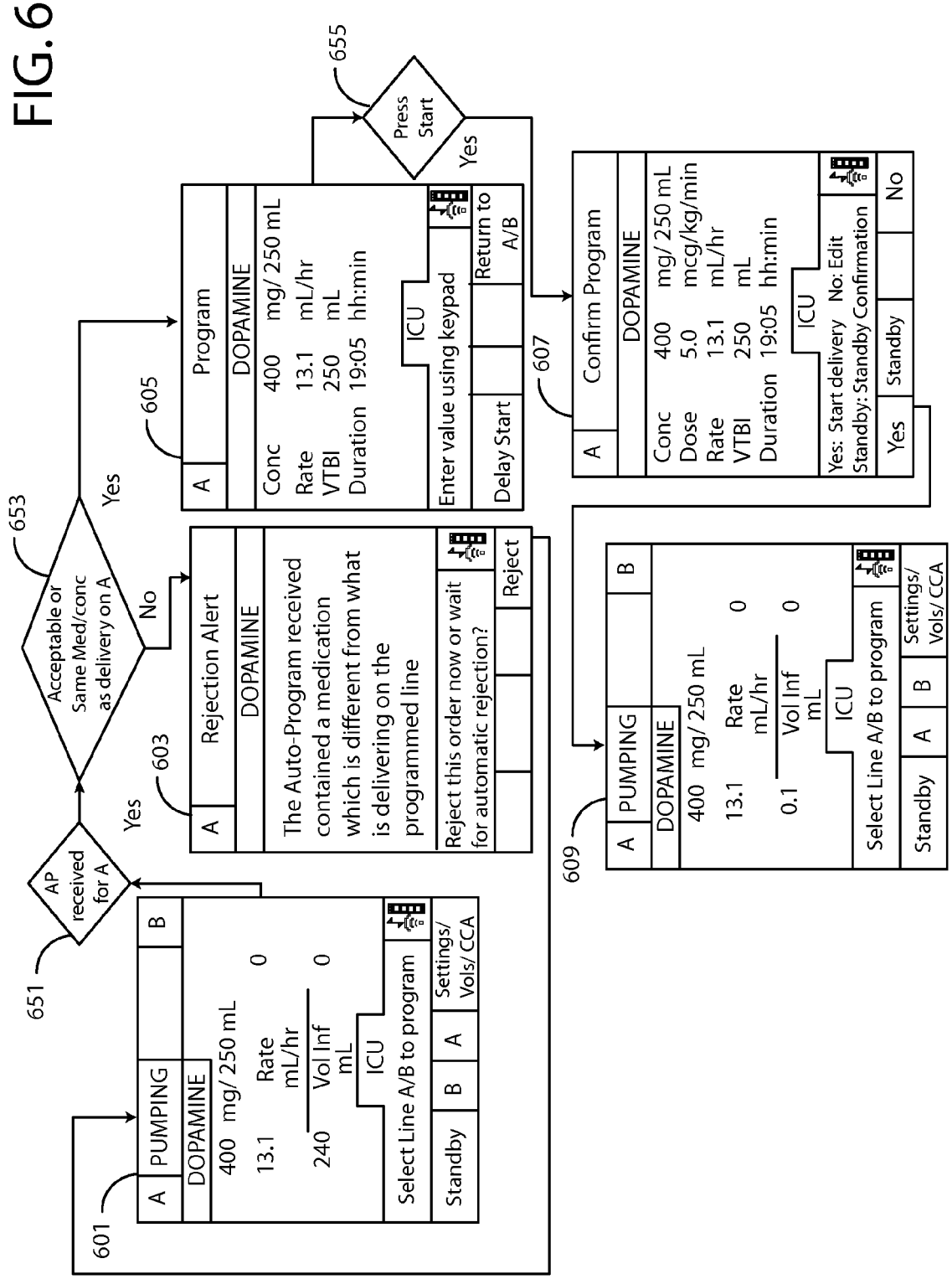

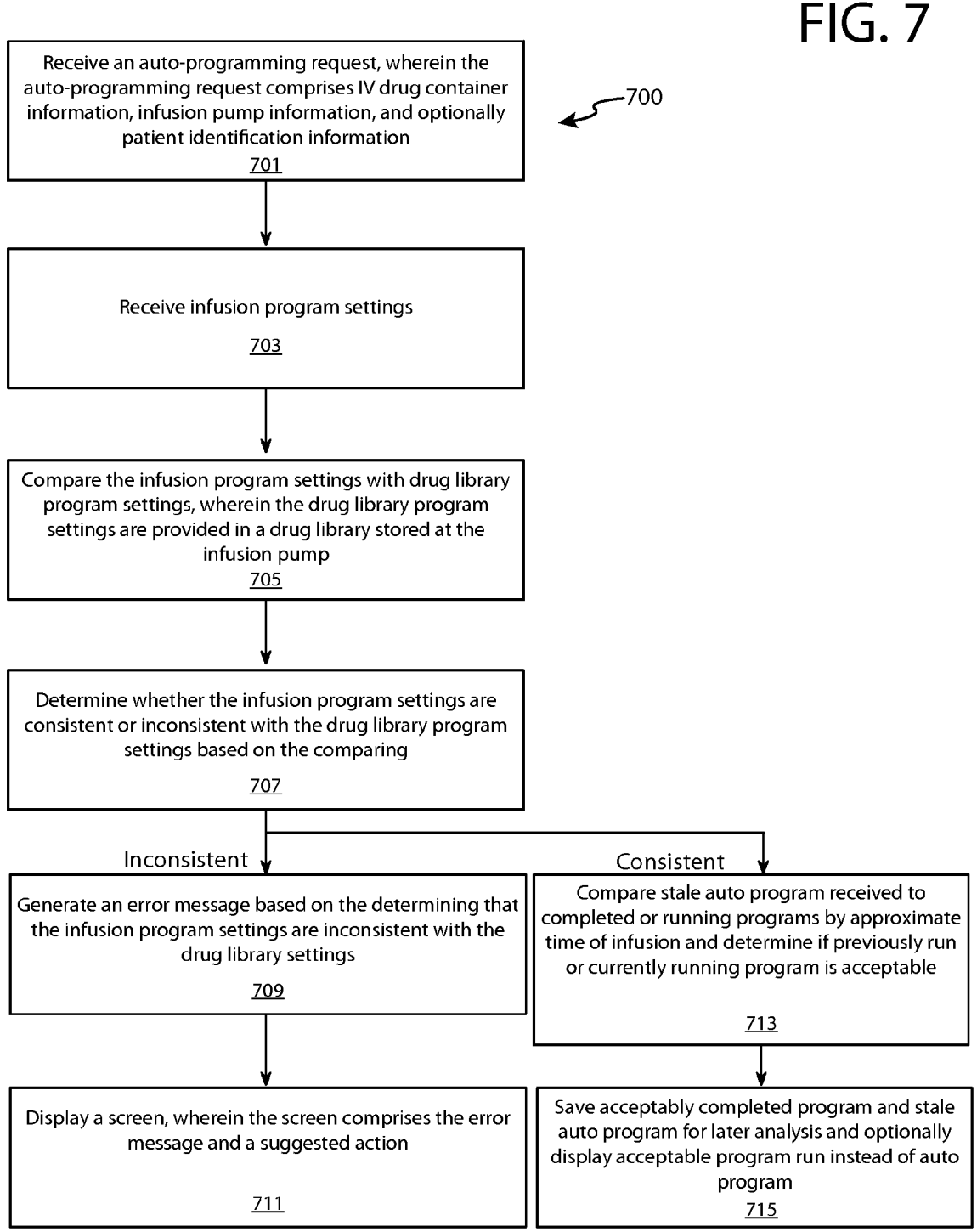

MATCHING DELAYED INFUSION AUTO-PROGRAMS WITH MANUALLY ENTERED INFUSION PROGRAMS

CROSS-REFERENCE TO RELATED APPLICATIONS

This application is a continuation of U.S. application Ser. No. 16/296,806, filed Mar. 8, 2019, now U.S. Pat. No. 10,799,632, which is a continuation of U.S. application Ser. No. 15/511,193, filed Mar. 14, 2017, now U.S. Pat. No. 10,238,799, which is the U.S. national stage of International Application No. PCT/US2015/050128, filed Sep. 15, 2015, which is a continuation of U.S. application Ser. No. 14/853, 198, filed Sep. 14, 2015, now U.S. Pat. No. 9,539,383, which claims the benefit of U.S. Application No. 62/050,536, filed Sep. 15, 2014, each of which is incorporated herein by reference in its entirety.

BACKGROUND OF THE INVENTION

Field of the Invention

The present disclosure relates to infusion pump programming analysis. Specifically, disclosed is a system and method that matches delayed infusion auto-programs with manually entered infusion programs and analyzes differences therein. At least one embodiment optionally displays an error message at the infusion pump if the manual or auto-program request is inconsistent with a drug library. At least one embodiment analyzes the differences in the manual program and the stale auto-program and saves the results of the analysis locally in the pump or remotely in a remote server for subsequent review and/or data mining.

Description of the Related Art

Infusion pumps are commonplace among medical devices in modern hospitals. The pumps serve as a useful tool for delivering medication to patients, and are particularly beneficial for their great accuracy in delivering medication at a specific rate and dose. Moreover, medical facilities have enabled hospital caregivers, such as nurses, to deliver medication to patients using auto-programming features available for the infusion pump. Although auto-programming features may reduce errors made manually by hospital caregivers, medical facilities still struggle with identifying and responding to errors made when using an infusion pump. In a conventional auto-programmable pump, error codes and messages may be sent surreptitiously from the pump to other areas of the medical network, but are not immediately accessible to a hospital caregiver submitting an auto-program request at the infusion pump. Furthermore, these error codes often do not specifically describe the error to the caregiver at the pump so that the caregiver may immediately respond to the error.

In addition, known systems do not analyze potential acceptable events if the manual program entered by the caregiver while waiting for an auto-program to arrive at the infusion pump is acceptable. Known systems do not store or analyze the differences between the manual program and the auto-program to determine response times, quality of data entry by the caregiver, and do not learn from caregivers that are at the point of care and thus may purposefully enter a different infusion rate or volume. Thus, there is a need for system and method that matches delayed infusion auto-programs with manually entered infusion programs and analyzes differences therein.

BRIEF SUMMARY OF THE INVENTION

The following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

Certain aspects disclose a method, comprising: receiving, at an infusion pump, an auto-programming request, wherein the auto-programming request comprises IV drug container information, infusion pump information, and optionally patient wristband information; receiving, at the infusion pump, infusion program settings; comparing, at the infusion pump, the infusion program settings with drug library program settings, wherein the drug library program settings are provided in a drug library stored at the infusion pump; determining, at the infusion pump, that the infusion program settings are inconsistent with the drug library program settings based on the comparing; generating, at the infusion pump, an error message based on the determining; and displaying, at the infusion pump, a screen, wherein the screen comprises the error message and a recommended action.

Certain other aspects disclose a non-transitory computer-readable storage medium having computer-executable program instructions stored thereon that, when executed by a processor, cause the processor to: receive an auto-programming request, wherein the auto-programming request comprises patient wristband information, IV drug container information, infusion pump information, and optionally patient wristband information; receive infusion program settings; compare the infusion program settings with drug library program settings, wherein the drug library program settings are provided in a drug library stored at the infusion pump; determine that the infusion program settings are inconsistent with the drug library program settings based on the comparing; generate an error message based on the determining; and display a screen on the infusion pump, wherein the screen comprises the error message and a recommended action; and receive a command in response to the error message and the suggested action.

Certain other aspects disclose an apparatus comprising: a memory; a processor, wherein the processor executes computer-executable program instructions which cause the processor to: receive an auto-programming request, wherein the auto-programming request comprises patient wristband information, IV bag information, infusion pump information, and optionally patient wristband information; receive infusion program settings; compare the infusion program settings with drug library program settings, wherein the drug library program settings are provided in a drug library stored at the infusion pump; determine that the infusion program settings are inconsistent with the drug library program settings based on the comparing; generate an error message based on the determining; and display a screen at the infusion pump, wherein the screen comprises the error message and a recommended action.

One or more embodiments of the invention include a system and method that identify delayed infusion programs at an infusion pump. At least one embodiment of the invention includes a first computer including a computer network interface and at least one infusion pump. In one or more embodiments, the first computer communicates with the at least one infusion pump via the computer network interface.

By way of one or more embodiments, the first computer receives at least one infusion auto-program from a remote source. In at least one embodiment, the remote source may include hospital information system, pharmacy information system or medication administration system and the first computer may include a medication management unit (MMU), such as a server equipped with Hospira MedNet™ software. In one or more embodiments, the at least one infusion auto-program may include one or more of IV drug container information, infusion pump information, and infusion program settings.

In at least one embodiment, the first computer transmits the at least one infusion auto-program to the at least one infusion pump. In one or more embodiments, the first computer may queue the at least one infusion auto-program when the first computer is unable to transmit the at least one infusion auto-program to the at least one infusion pump. In at least one embodiment, the first computer sends the at least one stale auto-program to the at least one infusion pump when the at least one infusion pump communicates with the first computer.

According to one or more embodiments of the invention, at least one infusion pump may receive at least one manual infusion program from a caregiver. In one or more embodiments, the at least one manual infusion program may include one or more of a completed manual infusion program or a running manual infusion program. In one or more embodiments, the at least one infusion pump saves and executes the at least one manual infusion program received from the caregiver, and compares the at least one stale auto-program to the at least one manual infusion program. In at least one embodiment of the invention, the at least one manual infusion program may be manually selected by a caregiver at the pump from a plurality of protocols that are predefined and provided in a drug library stored in the memory of the at least one infusion pump. In one or more embodiments, the comparison may be based on an approximate time of infusion administration and parameter matching logic including infusion administration parameters and infusion pump operating parameters.

By way of at least one embodiment, the at least one infusion pump compares the infusion pump operating parameters and the infusion administration parameters to identify potential matches between the at least one stale auto-program and the at least one manual infusion program. In one or more embodiments, the at least one infusion pump may evaluate the potential matches using one or more configurable rules and determines if the potential matches are within a predefined tolerance. In at least one embodiment, the at least one infusion pump may continue to execute the at least one manual infusion program on the at least one infusion pump if the potential matches are within the predefined tolerance.

In one or more embodiments, the at least one infusion pump saves differences in the at least one manual infusion program and the at least one stale auto-program locally in a processor of the pump and/or remotely in the remote server. In at least one embodiment, the at least one infusion pump locally and/or remotely saves a first event alert indicating the at least one manual infusion program as an acceptable potential match of the potential matches, and locally and/or remotely saves a second event alert indicating the at least one auto-program as an un-executed program because the at least one manual infusion program is an acceptable potential match.

According to at least one embodiment of the invention, the at least one infusion pump may include an input screen, such that the caregiver may input the at least one manual infusion program via the input screen.

In one or more embodiments, the at least one infusion pump may save identification data of the caregiver locally and/or remotely in the remote server. In at least one embodiment of the invention, the at least one infusion pump compares the at least one manual infusion program from the caregiver to the at least one stale auto-program to determine a scoring of accuracy. In at least one embodiment, the scoring of accuracy may include an acceptability level of the at least one manual infusion program from the caregiver.

By way of one or more embodiments of the invention, the at least one infusion pump may generate at least one report from the comparison of the at least one manual infusion program to the at least one stale auto-program. In at least one embodiment, the report generated by the at least one infusion pump may include one or more of a time differential between completion time of the at least one manual infusion program and completion time of the at least one stale auto-program, a scoring of accuracy including an acceptability level between infusion administration parameters of the at least one manual infusion program and the at least one stale auto-program, and a rating of the caregiver.

In one or more embodiments, the at least one infusion pump may transmit the at least one manual infusion program from the caregiver to the first computer. In at least one embodiment, the first computer may save the at least one manual infusion program from the caregiver and may save identification data of the caregiver. In one or more embodiments, the first computer may compare the at least one manual infusion program from the caregiver to the at least one stale auto-program to determine a scoring of accuracy. In at least one embodiment, the scoring of accuracy may include an acceptability level of the at least one manual infusion program from the caregiver, or analyze and save the program for review if the outcome for the patient results in improved care for example.

By way of one or more embodiments of the invention, the first computer may generate at least one report from the comparison of the at least one manual infusion program to the at least one stale auto-program. In at least one embodiment, the report generated by the first computer may include one or more of a time differential between completion time of the at least one manual infusion program and completion time of the at least one stale auto-program, a scoring of accuracy including an acceptability level between infusion administration parameters of the at least one manual infusion program and the at least one stale auto-program, and a rating of the caregiver. Data mining may be utilized to determine the manual programs that result in improved outcomes, less drug use, shorter patient stay or any other parameter.

The details of these and other embodiments of the disclosure are set forth in the accompanying drawings and description below. Other features and advantages of aspects of the disclosure will be apparent from the description, drawings, and claims.

BRIEF DESCRIPTION OF THE DRAWINGS

The above and other aspects, features and advantages of at least one embodiment of the invention will be more apparent from the following more particular description thereof, presented in conjunction with the following drawings wherein:

FIGS. 5 and 6 show illustrative flow diagrams for displaying error messages and acceptable manual programs at an infusion pump;

FIG. 7 shows an illustrative flowchart for displaying error messages and acceptable manual programs.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
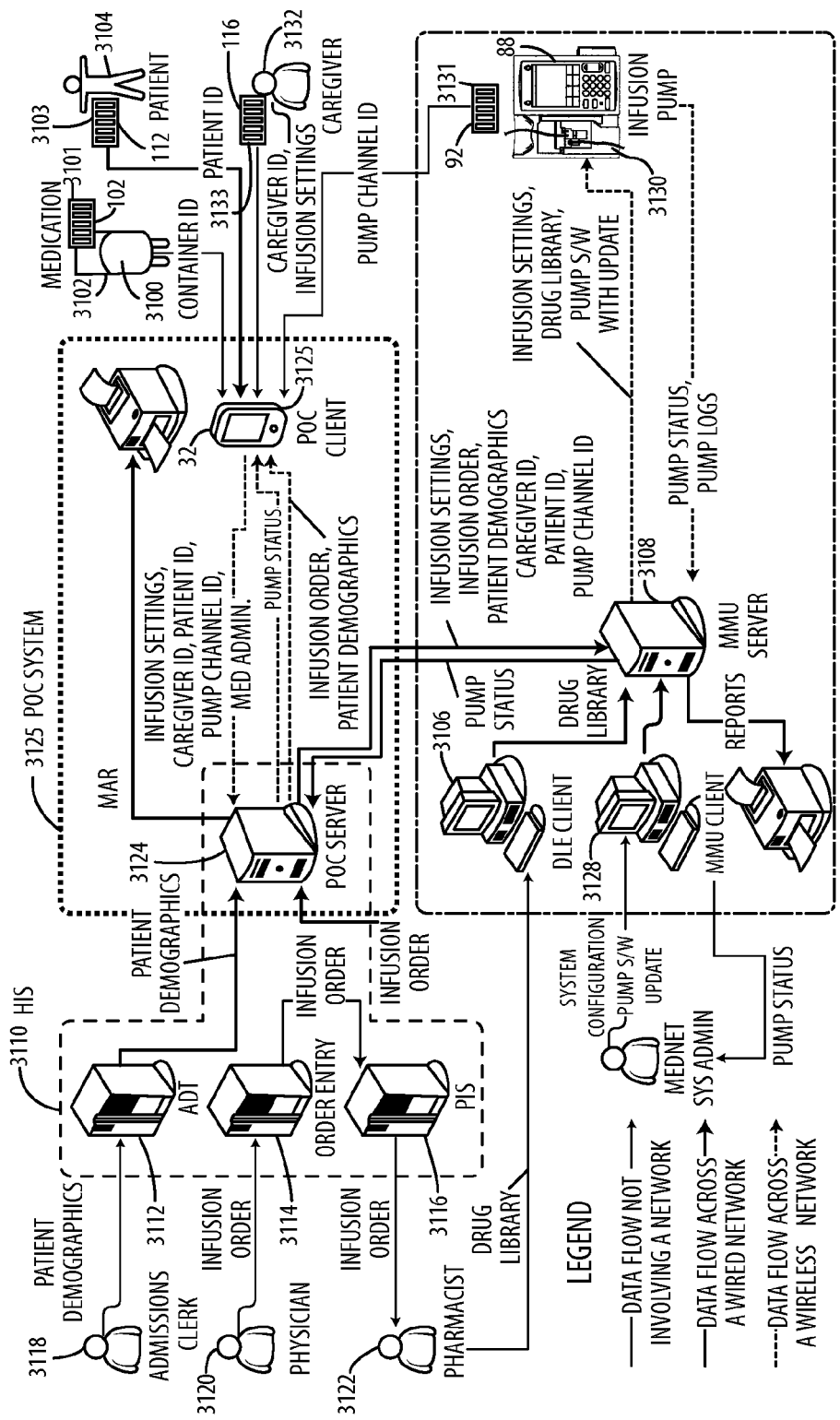
FIG. 1 shows an illustrative schematic diagram of a network for communication with an infusion pump.

FIG. 1 illustrates an exemplary schematic diagram of a system for administering medication via an infusion pump. The medication management system (MMS) shown in FIG. 1 comprises a medication management unit (MMU) 3108 and a medical device, such as infusion pump 3130, typically operating in conjunction with one or more information systems or components of a hospital environment.

Intravenous (IV) fluid(s) and/or medication(s) 3100 in containers 3102 may be administered to a patient 3104 using the system shown in FIG. 1. Although the system shown in exemplary FIG. 1 utilizes barcodes and a barcode reader as apparatus to input and read machine readable information, those skilled in the art will appreciate that other apparatus for reading or inputting information may be utilized. Machine readable indicia or identifying information may be provided by a transmitter, radio frequency identification (RFID) tag, or transponder and read by a radio frequency receiver or transceiver. The system may also utilize digital photography or imaging and scanning technology. Human biometric data, including retina patterns, voice, skin, fingerprints, and the like may also be recognized by an appropriate scanner or receiver. Moreover, POC client 3126 may comprise an identification receiver 32 adapted to recognize such indicia may be provided in the MMS.

In certain aspects, the IV fluids and/or medications 3100 in container 3102 may be provided with new or supplemental labels with a unique infusion order identifying barcode by a pharmacist according to certain hospital practices. Specifically, drug container specific identification information, such as barcoded information on the container 3102 may include patient identification information, including a patient name, patient number, medical record number for which the medication has been prescribed, medication identification information such as a medication name or solution within the IV container 3102, universal identification information which may be created or assigned at the hospital, medical device delivery information, such as the operating parameters to use in programming an infusion pump to deliver fluids and/or medication 3100 to the patient 3104, and/or medication order information, such as one or more of above information items and/or other medication order information specific to a particular patient 3104, and which may be a part of a medication order for a particular patient. The IV fluids and/or medications 3100 in barcode-identified containers 3102 may be supplied to hospitals by various vendors, with preexisting unique barcode identifiers which include medication information and other information, such as a National Disease Center (NDC) code, expiration information, drug interaction information, and the like.

In some aspects of the disclosure, the universal identification information on the container 3102 may be a unique medication order identifier that, by itself, identifies the order associated with the container. In other aspects, the identification information on the container 3102 may be a composite patient/order code that contains both a patient ID (such as a medical record number) and an order ID unique only within the context of the patient. In certain aspects, the identification information on the container 3102 may comprise a medication ID. Within a particular hospital, all medication prepared or packaged for patients by the pharmacy may contain either a composite patient/order ID or a universally unique order ID, but generally not within the same hospital. The medication ID alone option may be used only for medication that are pulled by a nurse directly from floor stock at the point of care.

The system identified in FIG. 1 may comprise a drug library editor (DLE) or DLE computer 3106, such as a notebook, desktop or server computer. The DLE computer 3106 may comprise DLE software that runs on the DLE terminal, computer or workstation 3106, shown as DLE Client in FIG. 1. As described above, a medication management unit (MMU) or computer 3108, such as a server, may have MMU software that is installed and runs on the MMU server 3108. The drug library and other databases may be stored on the MMU server 3108, a separate server, and/or in remote locations.

Hospital information systems (HIS) 3110 may include one or more computers connected by cabling, interfaces and/or Ethernet connections. Alternatively wireless connections and communications may be used in whole or in part. Servers provide processing capability and memory for storage of data and various application programs or modules, including but not limited to a module for admissions-discharge-and-transfer (ADT) 3112, a computerized physician order entry (CPOE) module 3114, and a pharmacy information system (PIS) module 3116. Hospital personnel, such as admission clerks 3118, physicians 3120, and pharmacists 3122, respectively, may be authorized to access these modules through client workstations connected to the servers in order to enter data, access information, run reports, and complete other tasks.

In the embodiment shown in FIG. 1, the HIS 3110 may also include a point of care (POC) system 3125 including a server or POC computer 3124 (sometimes referred to as a barcode point of care server or computer), or the POC computer 3124 may be separate from the HIS 3110. The POC computer 3124 may act as a part of a point of care (POC) system 3125 (sometimes referred to as the barcode point of care system or BPOC) and may be able to wirelessly communicate through a plurality of wireless communication nodes located throughout the hospital, utilizing a wireless communications protocol, such as IEEE 801.11, IEEE 802.11, or Bluetooth. The POC computer 3124 may communicate wirelessly with a portable thick client POC or input device 3126 carried by a caregiver. The POC client device 3126 may be a personal digital assistant (PDA) that comprises significant memory, display and processing capabilities. The POC client device may execute a variety of programs stored in its memory in some degree independently of the POC computer 3124.

In one embodiment of FIG. 1, the MMU server 3108 may be hard-wired to the DLE client desktop computer/workstation 3106 and to a MMU client computer/workstation 3128. Alternatively, the MMU and DLE client functions may be combined onto a single client computer/workstation or may reside together with the MMU server 3108 on a single combined MMU/DLE server. The MMU server 3108 may reside in a location remote from the patient's room or treatment area. For instance, the MMU server 3108 may reside in a secure, climate controlled information technology room with other hospital servers and computer equipment and its client terminals may be located in the pharmacy, biomedical engineering area, nurse station, or ward monitoring area. One MMU server 3108 may monitor, coordinate and communicate with many infusion pumps 3130. For example, in one embodiment, the MMU software running on the MMU server 3108 may support up to one thousand infusion pumps concurrently.

In embodiment of FIG. 1, the client PDA 3126 in the POC computer system 3125 may communicate through the POC server 3124 with the MMU server 3108. The MMU server 3108 may interface or communicate wirelessly with the infusion pump 3130 through the same wireless nodes 84 utilized by the POC system 3125 and a connectivity engine and antenna on or in the infusion pump 3130. Communication between the infusion pump 3130 and the POC client 3126 may take place through the MMU server 3108 and POC server 3124. The MMU computer 3108 may store in an associated memory both the logical ID and the network ID or Internet Protocol (IP) address of the infusion pump(s) 3130, such that only the MMU computer 3108 may communicate in a direct wireless manner with the infusion pump 3130. Alternatively the MMU 3108 may provide the IP address and other information about the pump 3130 to the POC system 3125 to facilitate direct communication between the POC system 3125 and the pump 3130.

Upon admission to the hospital, the admission clerk 3118 or similar personnel may enter demographic information about each patient 3104 into an associated memory of the ADT computer or module 3112 of an HIS database stored in an associated memory of the HIS system 3110. Each patient 3104 may be issued a patient identification wristband, bracelet or tag 112 (or other patient identification device) that may include an identifier 3103, such as a barcode or RFID tag for example, representing a unique set of characters, typically a patient ID or medical record number, identifying the patient, sometimes referred to as patient specific identification information. The wristband, bracelet or tag 112 may also include other information, in machine readable or human-readable form, such as the name of the patient's doctor, blood type, allergies, and the like as part of the patient specific identification information.

The patient's doctor 3120 may prescribe medical treatment by entering an order into the CPOE computer terminal or module 3120 within the HIS system 3110. The order, as prescribed, may specify a start time, stop time, a range of allowable doses, physiological targets, route, and site of administration. In the case of an order for infusion of fluids or medication, the order may be written in various formats, but typically includes the patient's name, patient ID number, a unique medication order or prescription number, a medication name, medication concentration, a dose or dosage, frequency, and a time of desired delivery. This information may be entered into the memory of the CPOE computer 3124, and may be stored in a memory associated with at least the POC server or computer 3124.

The medication order may also be delivered electronically to the PIS computer 3116 in the pharmacy and may be stored in an associated memory. The pharmacist 3122 may screen the prescribed order, translate it into an order for dispensing medication, and prepare the medication or fluids with the proper additives and/or necessary diluents. The pharmacist 3122 may prepare and affix a label 102 with drug container specific identifying information 3101 to the medication or drug container 3102. In one embodiment, the label only includes in machine-readable (barcode, RFID, etc.) form a unique sequentially assigned "dispense ID number" that may be tied to or associated with the particular patient ID number and medication order number in the HIS 3110, PIS 3116 and/or POC computer 3125. In another embodiment, the label may include in machine readable form a composite identifier that includes an order ID and a patient ID, which may be a medical record number. In another embodiment, the label does not include a patient ID at all in barcode or machine readable format but includes in machine readable form only a medication ID. Another embodiment may be useful for "floor stock" items that are commonly stocked in operating rooms, emergency rooms, or on a ward for administration on short notice with ad hoc or post hoc orders. In another embodiment, the label may include in machine readable and/or human-readable form medical device specific delivery information including but not limited to the dispense ID number, patient ID, drug name, drug concentration, container volume, volume-to-be-infused ("VTBI"), rate or duration, and the like. Only two of the three variables VTBI, rate and duration may be required to be defined as the third may be calculated when the other two are known. The labeled medication may be delivered to a secure, designated staging location or mobile drug cart on the ward or floor near the patient's room or treatment area. The medication order pending dispensing or administration may be posted to a task list in the HIS system 3110 and POC system 3125 and stored in an associated memory.

The caregiver 3132 (e.g., a nurse) may use the identification receiver 32 associated with the POC client 3126 to scan the caregiver specific identification information 3133 or barcode on his/her caregiver identification badge 116 (or other caregiver identification device) and enter a password, which logs the caregiver into the system and authorizes the caregiver to access a nurse's task list from the POC system 3125 through the POC client 3126. The information within the nurse's badge 116 is sometimes referred to as the caregiver specific identification information herein. The caregiver 3132 may view from the task list that IV drugs are to be administered to certain patients 3104 in certain rooms. The caregiver 3132 obtains the necessary supplies, including medications, from the pharmacy and/or a staging area in the vicinity of the patient's room.

The caregiver 3132 may take the supplies to a patient's bedside, turn on the infusion pump 3130, verify that the network connection icon on the pump 3130 indicates a network connection (for example, a wireless connection such as Wi-Fi or the like) is present, select the appropriate clinical care area (CCA) on the pump, and mount the IV bag, container, or vial 3102 and any associated tube set as required in position relative to the patient 3104 and infusion pump 3130 for infusion. Another connection icon on the pump 3130 or pump user interface screen can indicate that a wired or wireless connection to the MMU server 3108 is present. Using the identification receiver/reader integral to the POC client PDA 3126, the caregiver 3132 may scan the barcode on the patient's identification wristband, bracelet or tag 112 or other patient identification device. A task list associated with that particular patient may appear on the PDA 3126 screen. The task list, which may also include orders to give other forms of treatment or medication by other routes (oral, topical, etc.), may be obtained from the HIS via the POC server 3124 and communicated wirelessly to the POC client PDA 3126. In one embodiment, the list is generated by matching the scanned patient ID with the patient ID for orders in memory within the POC server 3124. In another embodiment, as will be described below, the order information may be obtained by scanning the drug container specific identification information for associated orders in memory within the POC server 3124, through the following step(s).

The caregiver 3132 may scan the medication barcode label 102 containing medication container specific identification information 3101 on the medication container 3102 with the PDA 3126. The PDA 3126 may highlight the IV administration task on the task list and send the scanned medication container specific identification information, such as dispense ID information, from the medication container 3102, to the POC server 3124, which uses the medication container specific identification information, such as the dispense ID, to pull together the rest of the order details and send them back to the PDA 3126. The PDA 3126 may then display an IV Documentation Form on its screen. One side of the IV Documentation Form screen may show the order details as "ordered" and the other side may be reserved for a status report from the infusion pump 3130. The status report from the infusion pump 3130 may be transmitted to the PDA 3126 through the POC server 3124 and MMU server 3108, as will be described below. The lower portion of the IV Documentation Form screen may provide the caregiver 3132 with instructions (like to scan the infusion pump 3130 barcode) or identify whether the pump is running or stopped.

The caregiver 3132 may then scan the barcode label 92 associated with the infusion pump 3130 (or pump channel if the pump is a multi-channel pump). The barcode label 92 may contain medical device specific identification information 3131, such as the logical name and/or logical address of the device or channel. The POC system 3125 then automatically bundles the information into a program pump request containing the "order details" and in one embodiment, without further interaction with the caregiver 3132, transmits this information to the MMU server 3108.

The program pump request may include at least some of the following information (in HIS/POC system format): a Transaction ID, which may include a Logical Pump ID, a Pump Compartment, a Pump Channel ID, a Reference Device Address, a Caregiver ID, a Caregiver Name, a Patient/Person ID (HIS identifier), a Patient Name, a Patient Birth Date & Time, a Patient Gender, a Patient Weight, a Patient Height, and an Encounter ID which may include a Room, a Bed, and a Building (including Clinical Care Area or CCA). The program pump request may also include Order Information or "order details", including an Order ID, a Start Date/Time, a Stop Date/Time, a Route of Administration, a Rate, a Duration of Infusion (Infuse Over), a Total Volume to be Infused (VTBI), an Ad Hoc Order Indicator, and Ingredients including HIS Drug Name or HIS Generic Drug Name, HIS Drug Identifier or HIS Generic Drug ID, Rx Type (Additive or Base), Strength w/units, and Volume w/units. The program pump request may further include Patient Controlled Analgesia (PCA) Orders Only information, such a PCA Mode-PCA only, Continuous only, or PCA and Continuous, a Lockout Interval (in minutes), a PCA Continuous Rate, a PCA Dose, a Loading Dose, a Dose Limit, a Dose Limit Time w/units, a Total Volume in vial or syringe, and Order Comments.

The MMU 3108 may map or convert the wide range of expressions of units allowed by the HIS system 3110 or POC system 3125 for PDA 3126 requests into the much more limited set of units allowed in the MMU 3108 and infusion pump 3130. For example, the PDA 3126 request may express "g, gm, gram, or grams" whereas the MMU 3108 and/or infusion pump 3130 may accept "grams" only. Infusion pump 3130 delivery parameters or infusion pump 3130 settings are mapped or converted from corresponding order information or "order details" of the program pump request.

The MMU 3108 may store in an associated memory a mapping or translation table that keep track of the logical ID, serial number or other identifier of an infusion pump 3130 and the corresponding current network (static or dynamic) address (Internet Protocol (IP) address) or ID of the infusion pump 3130 on the network, which in this example is a wireless network. The MMU 3108 may be able to translate or associate a given identifier of the infusion pump 3130 with its network address in the translation table and provide the network IP address to the requesting POC system 3125 or device. The MMU 3108 may also store in an associated memory and/or may look up the drug library applicable to the scanned infusion pump 3130 and may also convert the Drug ID and Strength from the pump program request into an index number of the medication at the desired strength or concentration from the drug library. The duration of the infusion may come from the POC system 3125 in hours and minutes and may be converted to just minutes for the infuser to recognize it. Volume or VTBI may be rounded to provide a value-specific and infuser-specific number of digits to the right of the decimal point. Units (of drug) may be converted to million units where appropriate. Patient weight may be converted and either rounded according to infuser-specific rules or not sent to the infuser.

Once the MMU 3108 transforms the information from the program pump request into infusion pump settings or delivery parameters and other information in a format acceptable to the infusion pump 3130, the MMU 3108 may wirelessly download a command message to the infusion pump 3130. If the infusion pump 3130 is not already equipped with the latest appropriate version of the hospital-established drug library, the MMU 3108 may also automatically download a drug library to the infusion pump 3130. The hospital-established drug library may be maintained in a separate process undertaken by the biomedical engineer or pharmacist 3122 to place limits on the programming of the infusion pump 3130, as well as other infusion pump operating parameters such as default alarm settings for air in the line, occlusion pressure, and the like. The drug library may set up acceptable ranges or hard and/or soft limits for various drug delivery parameters in the infusion pump 3130.

The MMU 3108 may also download to the infusion pump new versions, patches, or software updates of the infusion pump's internal operating system software. The infusion settings or delivery parameters and other information from the MMU 3108 may be entered into the memory of the infusion pump 3130 and the infusion pump 3130 settings may automatically populate the programming screen(s) of the infuser, just as if the caregiver 3132 had entered the information and settings manually. The infusion pump 3130 screen may populate with the name of the drug and drug concentration based on the drug library index number, patient weight (if applicable), rate, VTBI, and duration (only two of the last three variable are sent by the MMU 3108 because the pump 3130 may calculate the third from the other two). A return message of confirmation signal may be sent to the MMU 3108 by the infusion pump 3130 to indicate that the command message has been received. At this point, if necessary, the caregiver 3104 may manually enter any additional infusion settings or optional information that was not included in the command message.

The infusion pump 3130 may then prompt the caregiver 3132 to start the infusion pump 3130 by pressing the start button. When the caregiver 3132 presses the start button, a confirmation screen with the infusion settings programmed may be presented for confirmation and an auto-program acknowledgment message can be sent to the MMU server 3108 to forward without request (i.e., pushed in a near real-time manner) or provide to the POC system 3125 when requested or polled. When the caregiver 3132 presses the button to confirm, the infusion pump 3130 may begin delivering fluid according to the programmed settings. The infusion pump 3130 may send a status message to the MMU 3108 indicating that the infusion pump 3130 was successfully auto-programmed, confirmed and started by the caregiver 3132, and is now delivering fluid. This information may also be displayed at the infusion pump. The MMU 3108 may continue to receive logs and status messages wirelessly from the infusion pump 3130 periodically as the infusion progresses or when alarms occur.

The MMU 3108 may report a portion of the initial status message to the PDA 3126 through the POC server 3124 (in MMU format) to indicate that the infusion pump 3130 has been auto-programmed and the caregiver 3132 has confirmed the settings. The MMU 3108 may communicate to the POC system 3125 and/or at the infusion pump 3130 the actual Rate, VTBI and Duration. A notation at the bottom of the PDA screen and/or the infusion pump may indicate that the infusion pump 3130 is running. The infusion pump 3130 may compare and give a visual, audio or other type of affirmative signal if the pump information matches or acceptably corresponds with the ordered information. An initial determination of whether the pump information matches the order may be done in the MMU 3108 and communicated to the PDA 3126 through the POC server 3124. Alternatively, the POC server 3124 or the infusion pump 3130 may make the necessary comparisons. If the pump information does not match the order, the infusion pump 3130 at the display 88 may output a visual, audio or other type of negative signal, which may include an error message.

At least one embodiment of the invention includes a first computer, such as a medication management unit (MMU) 3108, including a computer network interface and the at least one infusion pump 3130. In one or more embodiments, the first computer communicates with the at least one infusion pump 3130 via the computer network interface.

By way of one or more embodiments, the first computer receives at least one infusion auto-program from a remote source. In at least one embodiment, the remote source may include a hospital information system, pharmacy information system or medication administration system and the first computer may include the medication management unit (MMU) 3108, such as a server equipped with Hospira MedNet™ software. In one or more embodiments, the at least one infusion auto-program may include one or more of IV drug container information, infusion pump information, and infusion program settings.

In at least one embodiment, the first computer transmits the at least one infusion auto-program to the at least one infusion pump 3130. In one or more embodiments, the first computer may queue the at least one infusion auto-program when the first computer is unable to transmit the at least one infusion auto-program to the at least one infusion pump 3130. In at least one embodiment, the first computer sends the at least one stale auto-program to the at least one infusion pump 3130 when the at least one infusion pump 3130 communicates with the first computer.

According to one or more embodiments of the invention, the at least one infusion pump 3130 may receive at least one manual infusion program from the at least one caregiver 3132. In one or more embodiments, the at least one manual infusion program may include one or more of a completed manual infusion program or a running manual infusion program.

The caregiver 3132 may be prompted to review and press a save button on the infusion pump 3130 if the order has been begun as desired or any variations are acceptable. The MMU 3108 may receive status, event, differences and variation information from the infusion pump 3130 and pass such information to the POC system 3125. In a separate subsequent step, the nurse may electronically sign the record and presses a send button on the POC client PDA 3126 to send the information to the patient's electronic medication record (EMR) or medication administration record (MAR).

Figure 2:
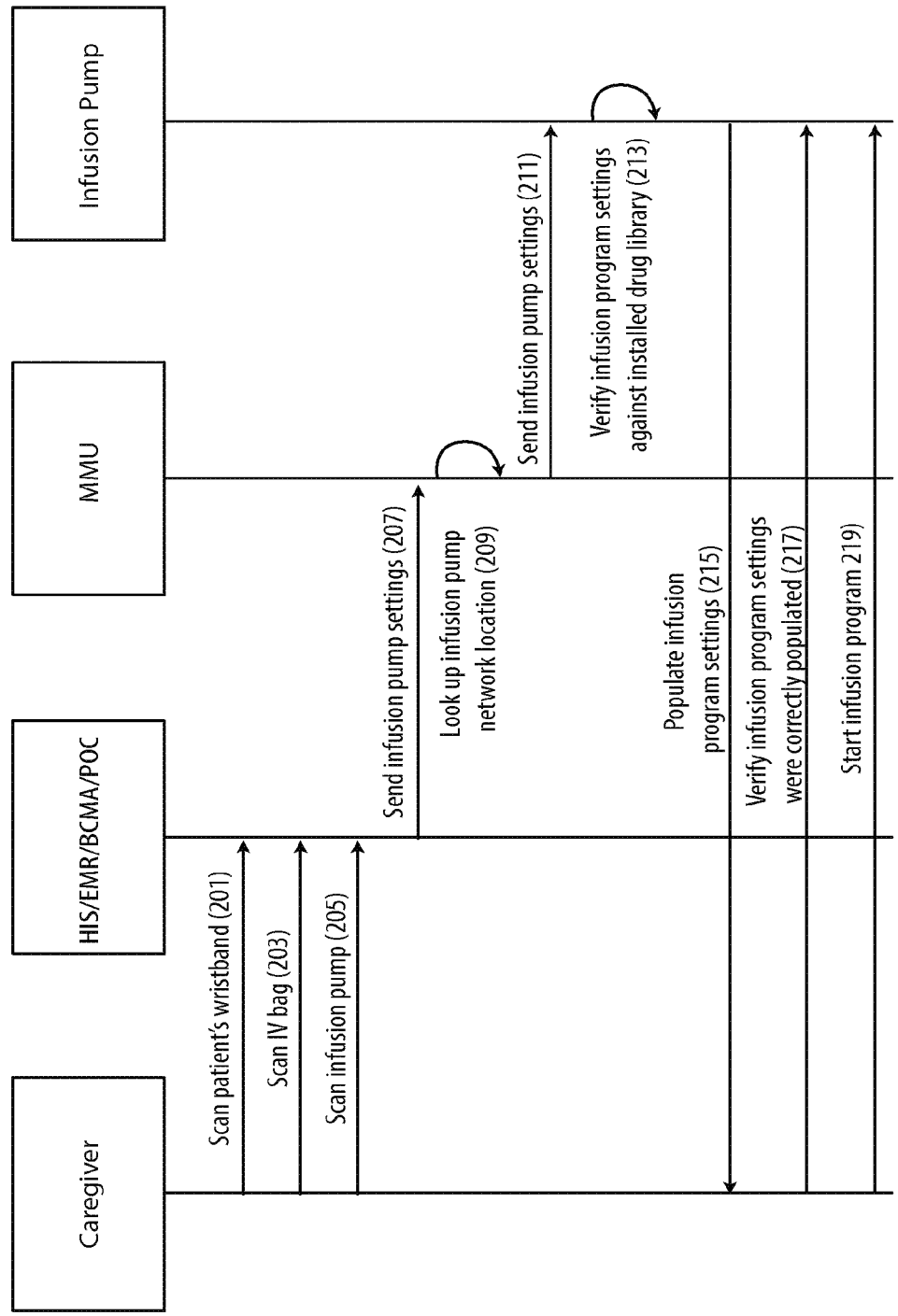
FIG. 2 shows an illustrative flowchart for auto-programming an infusion pump without an error being encountered.
Figure 3:
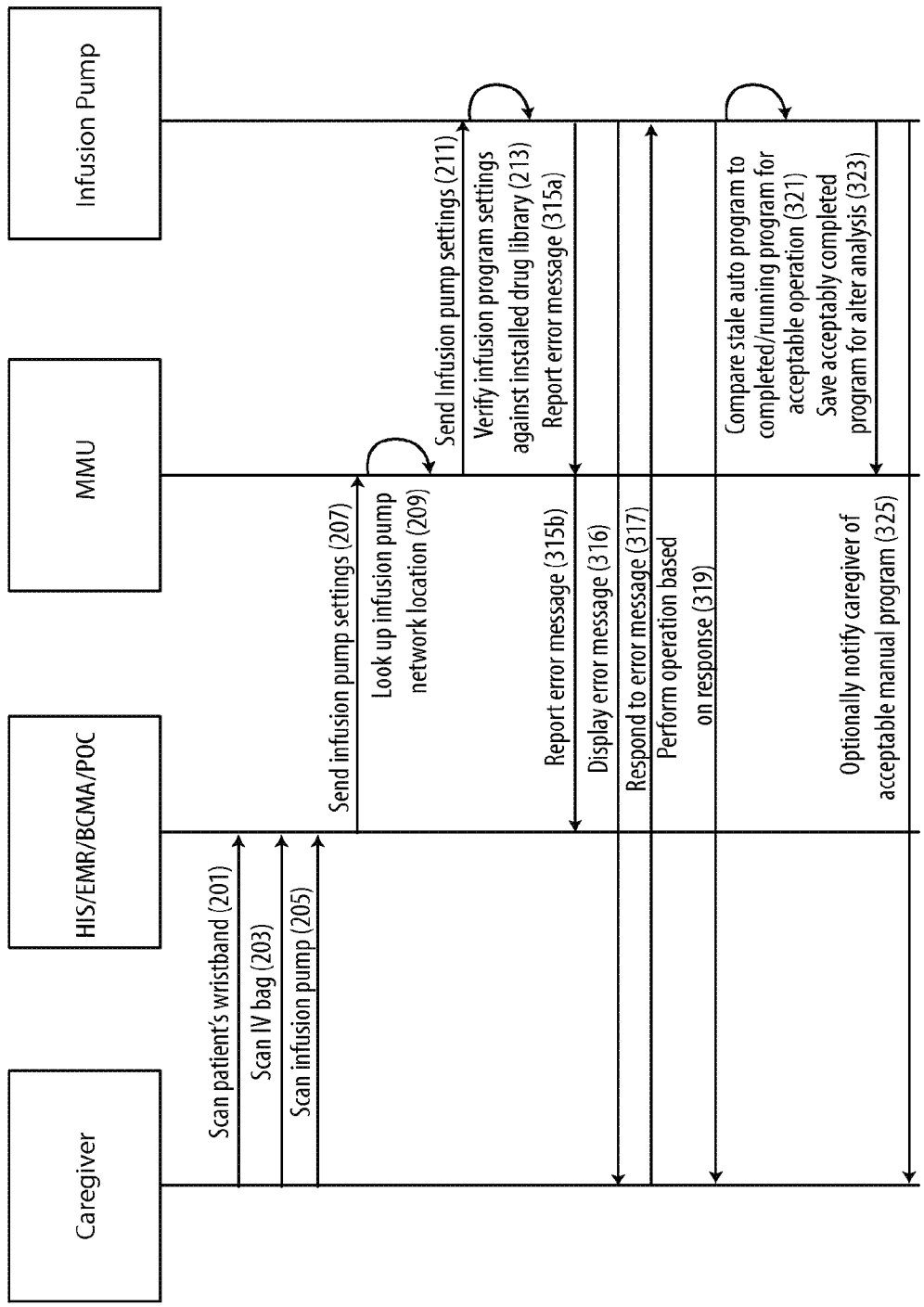
FIG. 3 shows an illustrative flowchart for auto-programming an infusion pump with an error being encountered and handled, and acceptable manual programs according to the present invention.

Referring now to FIGS. 2 and 3, flowcharts further illustrate a system and method for notifying a caregiver (e.g., caregiver 3132, such as a nurse) at an infusion pump 3130 of the status of administration of fluid and/or medication 3100 to a patient 3104 according to aspects of the disclosure. In one embodiment, the POC system 3125 sends a program pump message containing infusion pump settings to the MMU computer 3108, which looks up the targeted infusion pump 3130 according to its identifier and relays the infusion pump settings to the pump 3130. In another embodiment, when the POC system 3125 is auto-programming the infusion pump 3130, the POC system 3125, including the POC computer 3124 and/or the POC client 3126 may request the MMU 3108 for permission to program the infusion pump 3130. The MMU computer 3108 may grant this permission and then the POC system 3125 may communicate directly with the infusion pump 3130, without intervention by the MMU computer 3108. The MMU computer 3108 may continually receive asynchronous or synchronous near real-time status messages and event logs from the infusion pump 3130 and store this information in an associated memory for purposes of at least displaying infusion pump 3130 status and generating reports.

In certain aspects of the disclosure, prior to beginning the workflow illustrated in FIGS. 2 and 3, a caregiver 3132 may first be required to use POC system 3125 to scan an identifier of the caregiver's ID badge 116. The POC system 3125 may then determine if the caregiver 3132 is a valid POC system 3125 user. The POC system 3125 may also require the caregiver 3132 to enter a password, user name, and/or other information.

As shown in FIGS. 2 and 3, the caregiver 3132 may initiate the workflow for automatically programming the infusion pump 3130 by scanning the patient's wristband (step 201), scanning the IV bag (step 203), and scanning the infusion pump (step 205). At step 201, the caregiver 3132 may use a scanner, such as identification receiver 32 at POC client 3126, to scan the identifier on the patient's wristband, bracelet, or tag 112. The patient ID, which may be a medical record number, an account number or some other identifier that the care facility uses to positively identify the patient, may be retained in a memory in the POC client 3126.

At step 203, the caregiver 3132 may use the POC client 3126 to scan the identifier 3101 on the identification label 102 on the IV bag 3102. The container ID 3101 may comprise machine-readable indicia such as a bar code, RFID tag, or the like. The container ID 3101 may be a universally unique order ID so that the HIS 3110 or POC system 3125 may retrieve information about the association medication order without having to scan the patient ID on the patient wristband, bracelet, or tag 112 (or other patient identification device) or rely on such patient ID information for comparison purposes. Alternatively, the container ID may be a composite ID that includes patient ID or some portion thereof and an order ID related to that particular patient. Alternatively, the container ID may be an absolute or unique pharmacy order identifier that may be generated by the order entry or pharmacy information systems. Alternatively, for commonly used containers that are stocked on the ward or patient care floor, like dextrose, saline or other solutions, the container ID may be a medication ID that includes only medication-specific information, including but not limited to medication name, concentration (if applicable) and volume.

At step 205, the caregiver 3132 may use the POC client 3126 to scan the barcode label 92 or RFID tag on the infusion pump 3130 or a channel of the pump to obtain medical device specific identification information 3131 on the identifier. Thus, the POC client 3126 may receive or capture the pump ID or identifier information. Steps 201, 203, and 205 may be performed in any order. For instance, the caregiver 3132 may perform step 203 first, followed by steps 201 and 205, or may perform step 205 first, followed by steps 203 and 201, and the like.

As shown in FIGS. 2 and 3, the information scanned by the caregiver 3132 at steps 201, 203, and 205 may be transmitted to the patient's electronic medical records (EMR) and/or the barcode medication administration (BCMA). In certain aspects, the caregiver 3132, after performing the scans with the POC client 3126, may select a button (such as a "start" or "done" button) on the POC client 3126. Selection of the button may cause the POC client 3126 to transmit the scanned information to the EMR/BCMA. The BCMA may comprise, for example, POC system 3125.

Based on the received scanned information, the EMR/BCMA within the HIS 3110 may look up patient demographic information it received from the Admission, Discharge and Transfer (ADT) system 3112 and an infusion order for the patient or medication it received from the Pharmacy Information System (PIS) 3116. Software in POC system 3125 may then perform a variety of safety checks, comparisons or matching functions to ensure that the right drug is administered to the right patient, at the right rate, in the right dose, at the right time, via the right route, and by an authorized or right caregiver, etc. as is conventional in the BCMA art. The BCMA/POC system 3125 then transmits an auto-programming message containing infusion pump settings to the MMU 3108.

At step 209, based upon the pump identification information contained in the auto-programming message, the MMU 3108 may then look up the infusion pump network location to determine the pump that is targeted to receive the infusion pump settings contained in the auto-programming message.

At step 211, the MMU 3108 may send the infusion pump settings to the infusion pump 3130 using the pump's IP address. At step 213, the infusion pump 3130 may receive the infusion pump setting and then verify the infusion program settings against the installed drug library. In other words, the infusion pump 3130 may ensure that the received program settings for the patient 3104 are consistent with the information provided in the drug library. Steps 215, 217, and 219 shown in FIG. 2 illustrate exemplary steps that may be performed after the infusion pump has determined that the program settings are consistent with the permissible settings specified in the drug library of the pump 3130. As discussed further below, steps 315, 317, and 319 shown in FIG. 3 illustrate exemplary steps that may be performed after the infusion pump has determined that the program settings are inconsistent with the permissible settings specified in the drug library of the pump 3130.

As shown in FIG. 2, at step 215, after the infusion pump 3130 has verified that the program settings are consistent with the drug library, the infusion pump may populate the program settings, for example at display screen 88. The infusion pump 3130 may display one or more program settings at display screen 88, such as drug name, drug concentration, container volume, VTBI, rate or duration, and the like. The infusion pump 3130 may also display a request for a nurse to confirm the displayed program settings.

At step 217, the caregiver 3132 may review and verify that the displayed infusion program settings were correctly populated. The caregiver 3132, in some aspects, may be required to select a button at the infusion pump 3130 in order to indicate confirmation that the infusion program settings were correctly populated. In response, the infusion pump 3130 may display a start button on screen 88 that enables the caregiver 3132 to start the infusion in accordance with the final confirmed programmed pump settings. The caregiver 3132 may select the start button to start the infusion program at step 219.

Referring now to FIG. 3, workflow steps illustrate an exemplary process in which the infusion pump settings are inconsistent with the settings stored in the drug library. The process illustrated in FIG. 3 comprises the same steps 201, 203, 205, 207, 209, 211, and 213 as FIG. 2. However, the auto-programming workflow illustrated in FIG. 3 comprises exemplary steps 315, 317, 319, 321, 323 and 325 not performed at FIG. 2, and which may be performed after infusion pump 3130 determines that the infusion program settings are inconsistent with the drug library at step 213 or in the case of steps 321, 323 and 325, if the manual program is acceptable, yet perhaps not an exact match for a stale auto-program that arrives after or during a manual infusion for example. Embodiments generally analyze and save these events wherein the caregiver may also be notified that an auto-program has arrived, but that the caregiver has successfully manually programmed the infusion pump, whether exactly or acceptably when compared to the auto-program.

At step 315, infusion pump 3130 may display an error message. The error message may be reported to the MMU 3108 at step 315a. The error message may be relayed and reported to the EMR/POC system 3125 via the MMU server 3108 at step 315b. Alternative, the error message can be reported directly from the pump 3130 to the EMR/POC system 3125 through any wired or wireless networks available in the hospital. Most importantly, the error message may be displayed at or on the display screen 88 of infusion pump 3130. Thus, even if the caregiver has limited or no access to the POC client or other computer systems within the hospital at the time, they will be advised of auto-programming errors at the pump 3130. As will be discussed in greater detail below, the error message may notify the caregiver 3132 of the rejection of the auto-programming request. The error message may comprise an error code and a brief description of the error cause. The error message may further comprise suggested actions for the caregiver 3132 to perform in response to the error message. For example, if the keypad is locked, the infusion pump 3130 may output an error message KLO00017 stating "The auto-program is not valid because the keypad is locked." The infusion pump 3130 may also display, on the same screen, a suggested or recommended action, e.g., "Unlock the keypad". A table of errors, including exemplary code numbers, descriptions and recommended actions are included below in Table 1.

TABLE 1

Messages and Suggested Actions Relating to Auto-Programs

| Error Code | Message | Action |
|---|---|---|
| EPC00001 | Order rejected. Physician's order for an automatically programmed therapy exceeds the capabilities of the pump. | Recheck the order with pharmacy or physician. |
| HLV00002 | Order rejected. Physician's order for an automatically programmed therapy exceeds a hospital-defined drug library hard limit. | Recheck the order with pharmacy or physician. |
| NTA00003 | The auto-program received contains duration information, and you cannot titrate the duration of a delivery with this dosing unit(s). | Press [OK] now, or wait for this screen to automatically dismiss. |
| MRI00004 | The auto-program received did not contain all required information. | Press [OK] now, or wait for this screen to automatically dismiss. |
| SLV00005 | The auto-program received contains a value that exceeds a system limit. Or the values cause a calculated parameter to exceed a system limit. | Press [OK] now, or wait for this screen to automatically dismiss. |
| MCD00006 | The auto-program received contained a medication which is different from what is delivering on the programmed line. | Press [OK] now, or wait for this screen to automatically dismiss. |
| UPD00007 | The auto-program is for a line that contains unconfirmed programming data. | Resubmit the auto-program. All unconfirmed data will be cleared. |
| LIS00008 | The auto-program is for a line which is in Standby. | Clear this line and resubmit the auto-program. |
| LDS00009 | The auto-program is for a line which is in Delay Start. | Clear this line and resubmit the auto-program. |
| ACP00010 | The auto-program is for a line that has an active alarm that stops or prevents delivery, thus the auto-program is not valid in this alarm condition. | Clear alarm condition and resubmit the auto-program. |
| COV00011 | The auto-program is not valid due to concurrency violation. Delivery A + B greater than 500 mL/hr or less than 0.5 mL/hr for each line. | Press [OK] now, or wait for this screen to automatically dismiss. |
| NIB00012 | The auto-program is not valid for line B. The medication delivering on line A cannot be interrupted. | Press [OK] now, or wait for this screen to automatically dismiss. |
| NMW00013 | The auto-program is not valid because the weight in the auto-program does not match the weight on the program delivering on the other line. | Press [OK] now, or wait for this screen to automatically dismiss. |
| NMH00014 | The auto-program is not valid because the height in the auto-program does not match the height on the program delivering on the other line. | Press [OK] now, or wait for this screen to automatically dismiss. |
| NMB00027 | The auto-program is not valid because the BSA in the auto-program does not match the BSA on the program delivering on the other line. | Press [OK] now, or wait for this screen to automatically dismiss. |
| NCS00015 | The auto-program is not valid because a CCA has not been selected on the infuser. | Select a CCA and resubmit the auto-program. |
| NVD00018 | The auto-program is not valid because the received parameters will not result in a valid dose. | Press [OK] now, or wait for this screen to automatically dismiss. |

TABLE 1-continued

Messages and Suggested Actions Relating to Auto-Programs

| Error Code | Message | Action |
| --- | --- | --- |
| NDT00016 | The auto-program is not valid because the drug in the confirmed program was a "No Drug Selected" auto-program and titration is not allowed. | Press [OK] now, or wait for this screen to automatically dismiss. |
| ZVV00019 | The auto-program is not valid because the Rate cannot be titrated when VTBI is 0. | Press [OK] now, or wait for this screen to automatically dismiss. |
| NCP00020 | The auto-program is not valid because it is a titration for a line that has no confirmed program. | Press [OK] now, or wait for this screen to automatically dismiss. |
| KLO00017 | The auto-program is not valid because the keypad is locked. | Unlock the keypad. |
| MLV00021 | The auto-program is not valid for a line with a Multistep or Loading dose program. | Press [OK] now, or wait for this screen to automatically dismiss. |
| NIA00022 | The auto-program is not valid for line A. The medication in the auto-program is not interruptible and Line B is delivering a Piggyback infusion. | Press [OK] now, or wait for this screen to automatically dismiss. |
| ICD00023 | The auto-program for this infuser was rejected by Hospira MedNet due to incomplete or corrupt data. | Press [OK] now, or wait for this screen to automatically dismiss. |
| DLI00024 | The auto-program for this infuser was rejected by Hospira MedNet due to drug library incompatibility. | Press [OK] now, or wait for this screen to automatically dismiss. |
| PPL00025 | The auto-program is rejected because of a partially programmed line. | Press [Clear] and resubmit the auto-program. All unconfirmed data will be cleared. |
| ITP0026 | The auto-program is rejected because auto-programming is performed on a line in the PENDING or PUMPING state and the Post Infusion Rate (KVO or RATE) is interpreted as not being a titration. A pump with an installed cassette was started. The CCA was selected. Line A was programmed and delivery was started. A barcode was scanned and an order on line A was placed. The auto-program for line A was sent to the infuser. The infuser determines that the auto-program is a new delivery based on titration rules and rejects the auto-program. | Press [OK] now, or wait for this screen to automatically dismiss. |

At step 317, the caregiver 3132 may review and respond to the error message displayed at the infusion pump 3130. The caregiver 3132 may provide a response that comprises at least one of a modification to the auto-programming request, performing the actions suggested at the pump 3130, and/or rejecting or clearing the error message and suggested action. Based on the response to the error message received at step 317, pump 3130 may perform an operation at step 319. For example, after displaying the error message provided above and suggested action "Unlock the keypad", infusion pump 3130 may receive a response from the caregiver 3132 that the keypad has been unlocked. The caregiver's action of unlocking the keypad may itself serve as the response to the error message at step 317. Thereafter, the operation performed at step 319 may comprise the infusion pump starting the infusion program similar to or the same as step 219 illustrated in FIG. 2. Thus, if the caregiver 3132 responds to the error message at step 317 by performing the suggested action, the infusion pump 3130 may, at step 319, automatically start the requested infusion auto-program. The caregiver 3132 may respond to the error message by adjusting program settings such as dose, rate, VTBI, duration, and the like on the infusion pump 3130.

In some aspects, the caregiver 3132 may reject or override the error message displayed at step 315. The caregiver 3132 may override the error message at step 317 in cases of soft limit violations. Some limit violations may require entry of a special override code or input of a code from a second caregiver or supervisory personnel. In another aspect of the invention, the infusion pump 3130 may display an error message that a pump channel is "Already in Use". The caregiver 3132 may investigate and determine that the pump is not in use. The caregiver 3132 may send a response rejecting the error message and indicating that the pump channel is not currently in use. The pump 3130 may then return to step 213 to verify infusion program settings against the installed drug library or may automatically start the infusion program at step 219.

In certain aspects, the caregiver 3132 may not input a response into infusion pump 3130 within a predetermined time. The lack of a response within this predetermined time may itself server as a response to error message 317. Specifically, the infusion pump 3130 may be configured (for example, by the manufacturer or the hospital via the user customized drug library configuration settings downloaded to the pump by the MMU) to timeout after a predetermined time. The predetermined time may be about 15 seconds, 30 seconds, 35 seconds or any other amount of time. If the infusion pump 3130 does not receive a response within the timeout period (or predetermined time), the infusion pump 3130 may reject the auto-program and display a previous or home screen at display screen 88. In this case, the operation performed at step 319 may comprise clearing the error message and displaying a previous or home screen at the pump 3130.

In one or more embodiments, the at least one infusion pump 3130 saves and executes the at least one manual infusion program received from the at least one caregiver 3132. At step 321, in at least one embodiment, the at least one infusion pump 3130 compares the at least one stale auto-program to the at least one manual infusion program that has been completed or is running.

In at least one embodiment of the invention, the at least one manual infusion program may be entered at the infusion pump and/or accessed as provided in a library stored at the at least one infusion pump 3130. In one or more embodiments, the comparison may be based on an approximate time of infusion administration and parameter matching logic including infusion administration parameters and infusion pump operating parameters, for example volume to be infused, rate, or any other characteristic available in the system.

By way of at least one embodiment, the at least one infusion pump compares the infusion pump operating parameters and the infusion administration parameters to identify potential matches between the at least one stale auto-program and the at least one manual infusion program. In one or more embodiments, the at least one infusion pump 3130 may evaluate the potential matches using one or more configurable rules and determines if the potential matches are within a predefined tolerance. In at least one embodiment, the at least one infusion pump 3130 may continue to execute the at least one manual infusion program on the at least one infusion pump 3130 if the potential matches are within the predefined tolerance. Any type of logic including neural networks, rule based, threshold or range based may be utilized to determine whether an acceptable manual program has executed or is executing when compared with the stale auto-program.

At step 323, in one or more embodiments, the at least one infusion pump 3130 saves differences in the at least one manual infusion program and the at least one stale auto-program in the remote server or MMU 3108 for later analysis and/or data mining. This may allow the management system to determine which caregivers are accurate or even may be utilized to determine whether better outcomes of care result from a slightly different, yet acceptable manual program when compared to the auto-program as well as determine whether cost saving may be made while maintaining a given level of service, for example with shorter patient stays or less drug volume used overall. Any other large data analysis is in keeping with the invention when comparing manual programs and stale auto-programs and any parameters associated with the patient, drug, volume to be infused, rate, or any patient characteristics such as age or time of stay or any other parameter.

In at least one embodiment, the at least one infusion pump 3130 remotely saves a first event alert indicating the at least one manual infusion program as an acceptable potential match of the potential matches, and remotely saves a second event alert indicating the at least one auto-program as an un-executed program because the at least one manual infusion program is an acceptable potential match.

At step 325, in one or more embodiments, the at least one infusion pump 3130 may optionally notify the at least one caregiver 3132 of the acceptable at least one manual infusion program using the first event alert, and optionally notify the at least one caregiver 3132 of the at least one auto-program as an un-executed program using the second event alert.

According to at least one embodiment of the invention, the at least one infusion pump 3130 may include a graphical user interface comprising keys and a display screen 88 or an input/output touch screen 88 on the at least one infusion pump, such that the at least one caregiver 3132 may input the at least one manual infusion program via the graphical user interface.

In one or more embodiments, the at least one infusion pump 3130 may save identification data of the at least caregiver 3132. In at least one embodiment of the invention, the at least one infusion pump 3130 compares the at least one manual infusion program from the at least one caregiver 3132 to the at least one stale auto-program to determine a scoring of accuracy. In at least one embodiment, the scoring of accuracy may include an acceptability level of the at least one manual infusion program from the at least one caregiver.

By way of one or more embodiments of the invention, the at least one infusion pump 3130 may generate at least one report from the comparison of the at least one manual infusion program to the at least one stale auto-program. In at least one embodiment, the report generated by the at least one infusion pump 3130 may include one or more of a time differential between completion time of the at least one manual infusion program and completion time of the at least one stale auto-program, a scoring of accuracy including an acceptability level between infusion administration parameters of the at least one manual infusion program and the at least one stale auto-program, and a rating of the at least one caregiver 3132.

In at least one embodiment of the invention, the accuracy/effectiveness history or rating of the at least one caregiver 3132 may determine if the at least one manual infusion program received from said at least one caregiver 3132 is acceptable and/or more accurate or effective than the at least one auto-program. The at least one stale auto-program is aggregated and compared using matching logic (either statically residing on the pump or dynamically provided with the auto-program) to the at least one manual infusion program received from the at least one caregiver 3132 at the at least one infusion pump 3130. This comparison generates an auto-program compliance information/rating or contributes to an overall auto-program compliance information/rating for the at least one caregiver 3132. The at least one infusion pump 3130 would subsequently display the at least one caregiver 3132 compliance information (rating) for the at least one caregiver 3132 at the next attempt to auto-program the infusion pump. Auto-program compliance information is saved in a memory of the pump and, whether or not displayed on the pump, can be subsequently transmitted or relayed to the first computer, another medical device or infusion pump or a remote computer for storage, analysis, display or use.

In one or more embodiments, the at least one infusion pump 3130 may transmit the at least one manual infusion program from the at least one caregiver 3132 to the first computer. In at least one embodiment, the first computer may save the at least one manual infusion program from the at least one caregiver 3132 and may save identification data of the at least one caregiver 3132. In one or more embodiments, the first computer may compare the at least one manual infusion program from the at least one caregiver 3132 to the at least one stale auto-program to determine a scoring of accuracy or effectiveness. In at least one embodiment, the scoring of accuracy may include an acceptability level of the at least one manual infusion program from the at least one caregiver 3132.

By way of one or more embodiments of the invention, the first computer may generate at least one report from the comparison of the at least one manual infusion program to the at least one stale auto-program. In at least one embodiment, the report generated by the first computer may include one or more of a time differential between completion time of the at least one manual infusion program and completion time of the at least one stale auto-program, a scoring of accuracy including an acceptability level between infusion administration parameters of the at least one manual infusion program and the at least one stale auto-program, and a rating of the at least one caregiver 3132.

Figure 4:
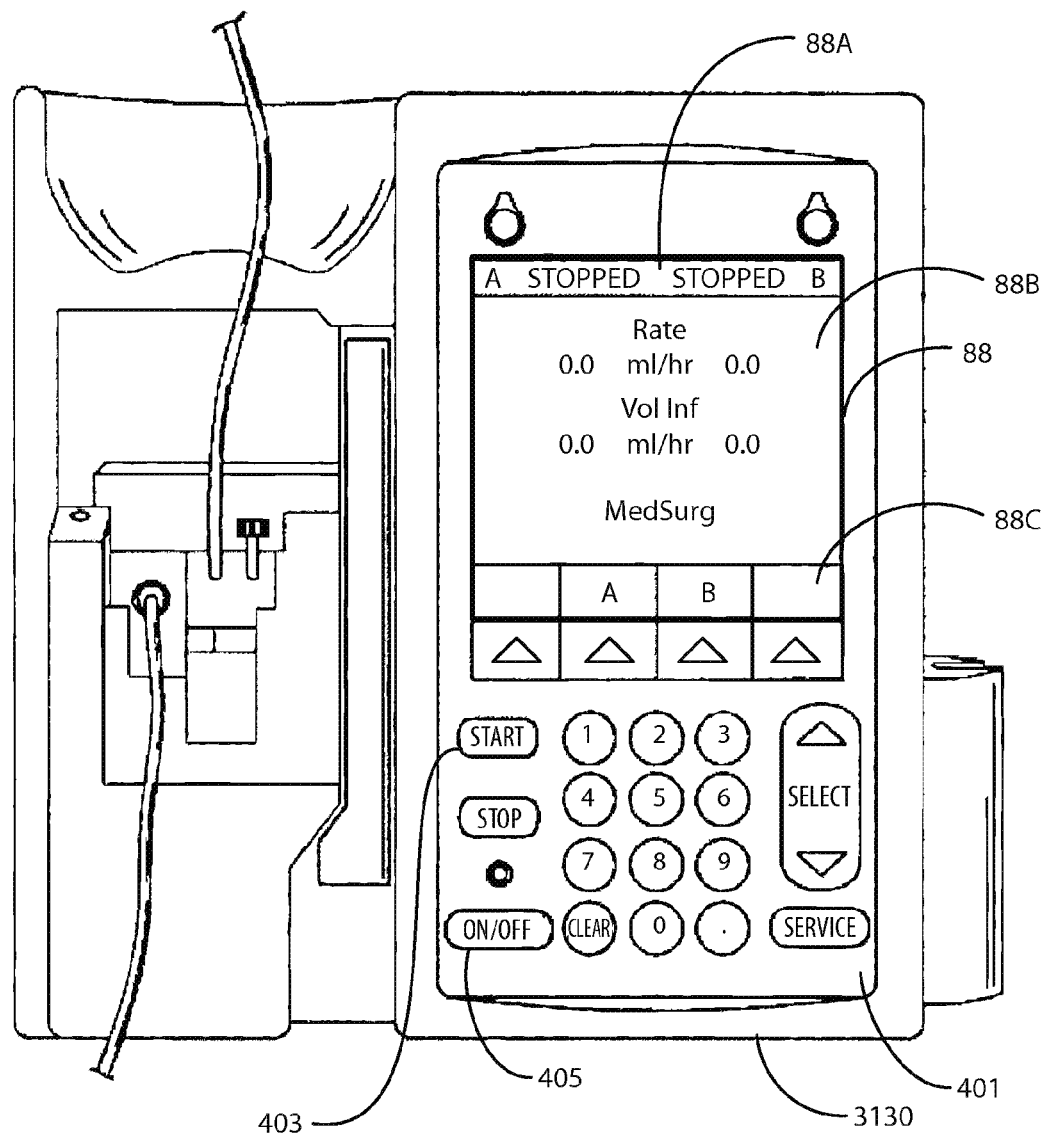
FIG. 4 shows an illustrative infusion pump.

FIG. 4 illustrates an enhanced view of the exemplary infusion pump 3130 comprising display screen 88. The exemplary screens provided in FIGS. 5 and 6 may be displayed at display screen 88. The infusion pump 3130 may display error messages, error codes, and suggested actions at display screen 88. The display screen 88 includes a plurality of areas or regions such as a status region 88A, a working region 88B, and a message region 88C. The pump may comprise a memory, a processor, a clock (real time or otherwise) and other components. The memory may store computer-executable program instruction. Moreover, the processor may execute the computer-executable program instructions, which may cause the processor to perform one or more steps recited in the present disclosure.

Figure 5:
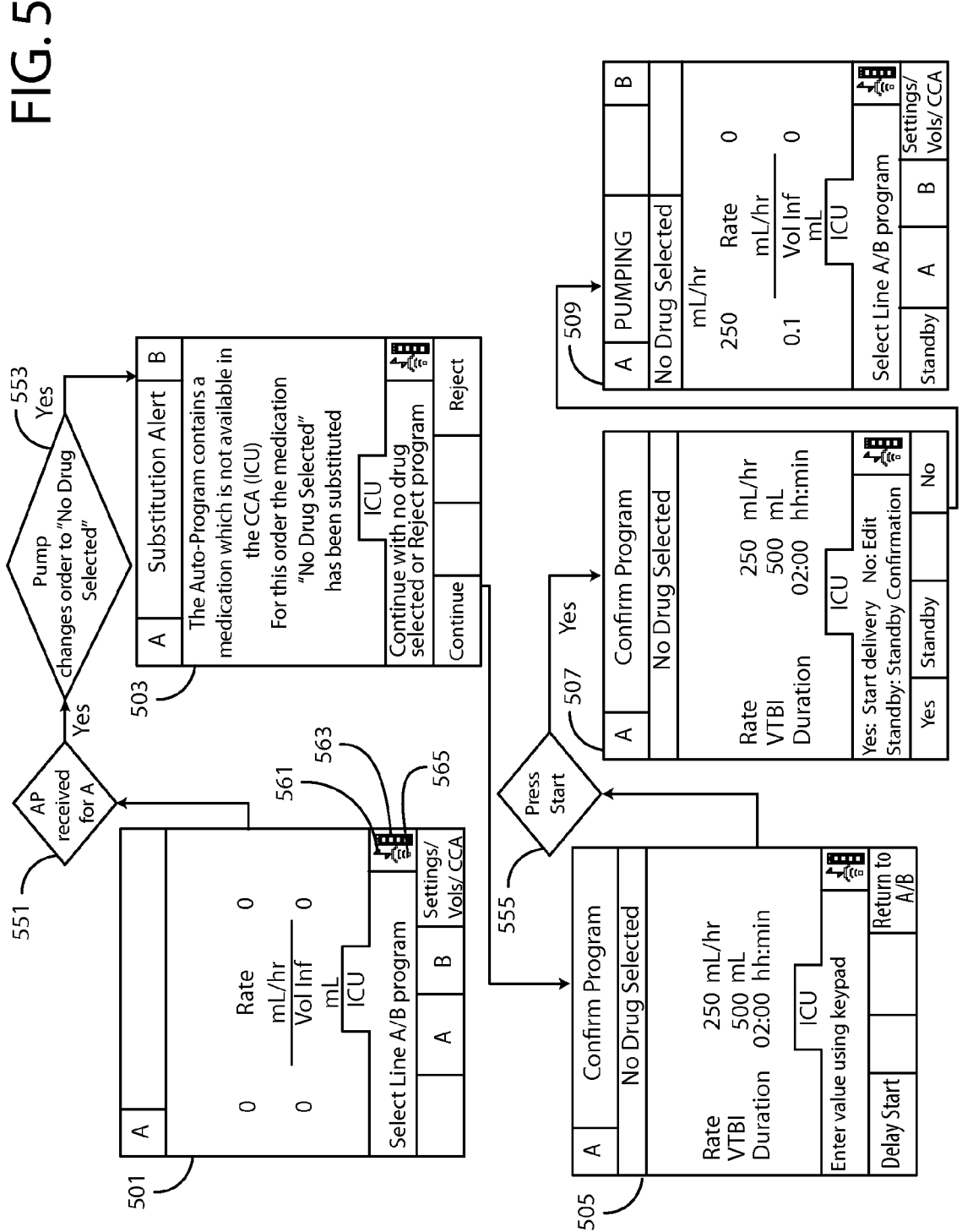

FIGS. 5 and 6 illustrate exemplary flow diagrams for displaying error messages at display screen 88. Prior to turning on the multi-channel infusion pump 3130, a cassette may or may not first be required to be installed in the infuser. A caregiver 3132 may install the cassette into the door of pump 3130 and then close the door. Next, the nurse may turn on the infusion pump 3130 by pressing an ON/OFF button, such as the ON/OFF button 405 shown in FIG. 4. After the ON/OFF button 405 is pressed, infusion pump 3130 may begin its startup process. After the startup process, which may take up to a few minutes, the infusion pump 3130 may be prepared to accept an auto-programming request.

At this point, infusion pump 3130 may display screen 501. Display screen 501 may be referred herein as the A/B screen or home screen. As shown in FIG. 5, screen 501 may display (in the working region 88B or elsewhere) delivery information for channel A and channel B, such as the rate and volume infused or volume to be infused (VTBI). Because an auto-programming request has not yet been received, the initial values for the delivery information may be set at 0 as shown in screen 501. The home screen 501 may also display a selected CCA (here shown directly below the Volume Infused or Volume To Be Infused (VTBI) as "ICU," which represents an intensive care unit). Home screen 501 may also display instructions or suggested actions that could be taken by a caregiver 3132. For example, screen 501 may initially display suggested action "Select Line A/B to program" as shown in FIG. 5. The suggested action may alert the caregiver 3132 of the next steps to be taken in order to submit a manual or an auto-program request. In certain aspects, infusion pump 3130 may display the suggested actions at screen 88 in a different color and/or with different shading than other information displayed on the screen. Exemplary screens shown in FIGS. 5 and 6, for example, display the suggested actions in white text with black shading in contrast to other information displayed in black text and white shading. Moreover, the suggested actions may be displayed in a particular section, region or area of each screen, such as in the message region near the bottom of each screen shown in FIGS. 5 and 6.

The screens displayed at the infusion pump 3130 may include other indicators, such as a battery life indicator 563 (which may indicate the amount of battery life remaining for the pump 3130), a wireless signal indicator 565 (which may indicate the strength of the wireless signal connection at pump 3130), and a two-way arrow 561 (which may indicate connection between the MMU and the pump and thus the capability of pump 3130 to upload and download information to and from the MMU server 3108).

Screens, as shown in FIGS. 5 and 6, may further comprise various input options. The input options may be presented in a row at the bottom of the screen (such as directly below the suggested actions as shown in FIGS. 5 and 6). Each input option may be an option that may be selected by a caregiver 3132. In some aspects, the caregiver 3132 may touch the screen itself to select an input option, and in other aspects, the caregiver 3132 may select a corresponding soft key or button directly below the input option. See the triangles below the screen 88 and the input options in FIG. 4. Other options and text, such as "OK", "Continue", "Reject", "Yes", "No", "Standby", "Standby Confirmation", "Delay Start", "Return to A/B", etc. may be displayed in the message region 88C and selected by caregiver using a touchable screen or the corresponding soft key below the displayed option or text. In response to the display at screen 501 and the suggested action "Select Line A/B to program", caregiver 3132 may select either input option "A", input option "B", or input option "Settings/Vols/CCA". Selecting option "Settings/Vols/CCA" may cause infusion pump 3130 to display a screen in which caregiver 3132 may edit settings, the way volume is displayed (volume infused versus volume to be infused or VTBI), or a CCA for the infusion pump 3130. Selecting either option "A" or "B" may initiate the auto-program sequence for that selected channel.

At step 551, infusion pump 3130 may determine whether an auto-programming request has been received. In other words, infusion pump 3130 may determine whether the steps described with respect to FIGS. 1-3 have been performed, particularly steps 201, 203, 205, 207, 209, and 211.

At step 553, the infusion pump 3130 may determine whether it needs to change the auto-program drug order to "No Drug Selected". The analysis performed at step 553 is an example of the various analyses that may be performed when the infusion pump 3130 verifies the infusion program settings against the installed drug library at step 213. Thus, as the pump 3130 performs its verification step 213, one of the plurality of verification actions it may perform may include determining whether the medication selected by caregiver 3132 is stored in the drug library for the selected CCA. For example, caregiver 3132 may select the CCA "ICU" prior to auto-programming. Then the caregiver 3132 may select or scan medication using POC client 3126 at step 203. After pump 3130 receives the auto-programming request for the ICU CCA, pump 3130 may verify the program settings against installed settings stored in its drug library at step 213. One of the verification steps may include determining whether the selected or scanned medication is included among the medications stored in the drug library for the ICU CCA. In other words, a processor of the pump 3130 makes a comparison between the drug name, concentration and dosing units provided in the auto-programming request to the same parameters in the drug library for the particular clinical care area selected or active on the pump. If, in the drug library, the selected medication is not among the listed medications available for the ICU CCA, pump 3130 may be programmed to output "No Drug Selected" as a substitution alert error message. At step 553, if the pump 3130 determines that it must change the order to "No Drug Selected", it may display an error message such as screen 503.

The error message may comprise a brief description of the error so that the caregiver 3132 may be able to quickly determine the cause of the error at the pump 3130 and perform subsequent actions in response to the error. In the example provided at screen 503, processor of the pump 3130 may perform a drug name, concentration, dosing units, or drug ID comparison against the drug list in the drug library on the pump for the selected clinical care area or CCA and display at display screen 88 the error message "The Auto-Program contains a medication which is not available in the CCA (ICU)" and "For this order the medication 'No Drug Selected' has been substituted". The pump 3130 may display a "Substitution Alert" in the status region or elsewhere on screen 503 to notify caregiver 3132 that an error has occurred. The error message may then notify the caregiver 3132 of the precise cause of the error (here, the selected CCA and the fact that the auto-program contained a medication that, pursuant to the hospital's best practices as set forth in the customizable drug library, is not planned to be available in the CCA). The error message may also, in some aspects display the actions taken by the pump 3130 in response to the error (here, "No Drug Selected" has been substituted for the medication by the processor of the pump because it found no match for the medication in the drug library entries for the selected CCA).

Also shown in the message region or elsewhere on the screen 503 is the suggested action "Continue with no drug selected or Reject program". The suggested action may notify caregiver 3132 that s/he should either select the input option "Continue" in order to continue the auto-program request with no drug selected substituted for the medication, or select the input option "Reject" to cancel the auto-program request. The input options may be displayed immediately below the suggested action, as shown in screen 503. If the caregiver 3132 selects the "Reject" option, pump 3130 may deny the auto-program request and display a previous screen such as home screen 501. A message concerning the rejection of the auto-program request may be sent to the MMU server 3108, which then relays the message to the POC system 3125. In certain aspects, screen 503 may be displayed for a predetermined amount of time, such as about 30 seconds. If no response or input option is selected within that predetermined amount of time, pump 3130 may automatically reject the auto-programming request and display screen 501. If, instead, the caregiver 3132 selects the "Continue" input option, pump 3130 may display screen 505 where the rest of the auto-programmed delivery information is pre-populated on the pump screen 88 in the working region 88B or elsewhere as shown on screen 505. At screen 505, caregiver 3132 may edit the delivery information, such as rate, VTBI, and duration. Screen 505 may continue to display "No Drug Selected" in or near the status region 88A at the top of the screen and a suggested action "Enter value using keypad" in the message region 88C at the lower portion of the screen 88. Pump 3130 may also highlight the field that may have its value edited (here, e.g., "500" for VTBI in mL) or do so when activated by touch or other keys. The caregiver 3132 may enter these values on the keypad 401 provided at the pump 3130, as shown in FIG. 4.

At step 555, pump 3130 may determine if the start button 403 (FIG. 4) has been selected or pressed by the user. If so, pump 3130 may display a screen such as screen 507. The screen 507 may correlate with step 217 in which the caregiver 3132 verifies the infusion program settings were correctly populated. Caregiver 3132 may select input option "No" to return to screen 505 and edit one or more of the displayed delivery information values. Alternatively, caregiver 3132 may select the "Standby" input option to standby for a predetermined or configurable period of time to await confirmation of the medication delivery. If the "Yes" input option is selected, pump 3130 may start the infusion program at step 219 and may display screen 509. Screen 509 may notify the caregiver 3132 that medication is pumping on the selected channel (here, channel A) at the selected rate (here, 250 mL/hr) and display a current Volume Infused (here, 0.1 mL). Screen 509 may also display the suggested action "Select Line A/B to program", which may enable the caregiver 3132 to edit or submit another auto-program request for channel A or B. In certain aspects, channel A may be a primary channel for administering medication and channel B may be a secondary line for administering medication.

FIG. 6 illustrates another example of a flow diagram of screens displayed at pump 3130. The series of screens shown in FIG. 6 begins at screen 601, which may be similar to screen 509 shown in FIG. 5. In the example provided in FIG. 6, a caregiver 3132 may request an auto-program at pump 3130 even as channel A is pumping. Here the pump 3130 is pumping Dopamine, a commonly prescribed vasoactive medication for controlling blood pressure. Dopamine is prescribed based on the patient's weight, which in this example is 70 kg. The Dopamine is supplied at a concentration of 400 mg in a 250 mL container. The prescribe dose is 5.0 mcg/kg/min, which the pump converts to a rate of 13.1 mL/hr. The pump 3130 has pumped 240 mL so far. Similar to step 551 of FIG. 5, the pump 3130 may determine in step 651 whether an auto-programming (AP) request has been received for channel A. The request may be received after steps 201, 203, 205, 207, 209, and 211 have been performed. At step 213, pump 3130 may verify infusion program settings against program settings stored in the drug library. In some aspects, pump 3130 may further verify the infusion program settings against settings hard-coded into the pump. The verification step 213 of FIG. 2 or FIG. 3 may comprise step 653 of FIG. 6, in which pump 3130 may determine whether the auto-program request for channel A is for the same medication or an acceptable alternative to the medication currently being delivered at channel A. In one aspect, the concept of the "same medication" can comprise the same medication by name (generic or brand), and one or more of concentration and dosing units. If the medication in the auto-program request for channel A is Dopamine, it might be okay and not trigger a mismatched medication/concentration error (code MCD00006 in Table 1 above). However, if the pump determines in step 653 that a different or non-equivalent medication is specified in the auto-program request received in step 651, such as Morphine for example, the pump 3130 displays the error message shown on screen 603.

Screen 603 may display "Rejection Alert" in the status region or another region of the screen to notify caregiver 3132 of an error. Screen 603 may also display the error message, such as "The Auto-Program received contained a medication which is different from what is delivering on the programmed line" in the working region or another region. Thus, the caregiver 3132 may be notified at the pump 3130 that there has been an error and the cause of the error. In some aspects, this error message may also display the medication that is being delivered on the channel, and/or other information such as the concentration and or dosing units of the medication order. For example, the error message at screen 603 may display "The Auto-Program received contained a medication [Morphine] which is different from [Dopamine] that is delivering on the programmed line" or "The Auto-Program received contained a medication which is different from the [Dopamine 400 mg/250 mL] that is delivering on the programmed line". Screen 603 may also display the suggested action for this error message in the message region or another region, in this case "Reject this order now, or wait for automatic rejection?" Pump 3130 may provide one or more one input options at screen 603, e.g., an option to reject the auto-program order. Caregiver 3132 may select the "Reject" option to return to screen 509. Alternatively, caregiver 3132 may not select an input option at all, in which case pump 3130 may automatically reject the auto-program order after the timeout period, such as about 30 seconds.

If, at step 653, pump 3130 determines that the medication in the auto-programming request is the same or equivalent as the medication currently pumping on channel A, or that the at least one manual infusion program is acceptable, pump 3130 may display screen 605. Similar to screen 505, discussed above, screen 605 may enable a caregiver 3132 to modify the settings of the delivery information values, such as concentration, rate, VTBI, and duration. Also shown at screen 605 is an input option "Delay Start". A caregiver 3132 may select the "Delay Start" input option in order to select a later time in which to begin pumping of the auto-program medication. Alternatively, caregiver 3132 may select the "Return to A/B" input option to return to screen 509.

At step 655, pump 3130 determines if the start button 403 (as shown in FIG. 4) has been selected. If so, pump 3130 may display screen 607. Caregiver 3132 may be able to review the information displayed at screen 607, similar to screen 507 as discussed above. Caregiver 3132 may then select the "Yes" input option to verify that the infusion program settings were correctly populated at step 217. In response, pump 3130 may start the infusion program at step 219 and the infusion pump 3130 may display screen 609.

Some other examples of error messages that may be displayed by the pump 3130, for example at screens such as screens 503 and 603, will now be discussed in further detail. In certain aspects, pump 3130 may determine an error at step 213 without any outside intervention from, for example, MMU, HIS, BCMA, EMR, and the POC system. In some cases, pump 3130 may allow an auto-programming order to continue after displaying an error message. Pump 3130 may also notify parties, such as MMU, HIS, BCMA, EMR, and the POC system of an error and the error message that was displayed. Those of ordinary skill in the art will appreciate that the error messages disclosed herein are exemplary, and may be modified without veering from the scope of this disclosure.

Pump 3130 may display an error message such as associated with error code NTA00003 in Table 1 above, "The auto-program received contains duration information, and you cannot titrate the duration of a delivery with this dosing unit". This error message will be displayed when the infuser receives an auto-program message with a titrated duration value and is for a medication that normally has time-based alternative dosing units. For example, if the drug involved in the program has time-based alternative dosing units the caregiver is not allowed to change the duration because such an action would change the associated dose. Examples include but are not limited to vasoactive drugs like nitroglycerin or Dopamine dosed in mcg/kg/min, anti-coagulants like Heparin dosed in units/kg/hour, diabetes control drugs like Insulin dosed in Units/kg/day, and oncolytic drugs like Taxol dosed in mg/m2/day. The particular drugs or categories of drugs for which this type error is generated can be established by the hospital according to their preferences in their user customizable drug library. On the same screen, pump 3130 may display the suggested action, e.g., "Press OK now, or wait for this screen to automatically dismiss". After selection of the "OK" input option or waiting for the screen to automatically dismiss after the timeout period, pump 3130 may display the home A/B screen.

In some aspects of the disclosure, pump 3130 may display an error message such as "The auto-program received did not contain all required information". Generally, the auto-programming message should include at a minimum the following information: pump channel, drug name and concentration. If one or more of these elements, parameters or settings is missing, the above-mentioned error message is displayed. On the same screen, pump 3130 may display the suggested action, e.g., "Press OK now, or wait for this screen to automatically dismiss". As discussed above, after selection of the "OK" input option or waiting for the screen to automatically dismiss after the timeout period, pump 3130 may display the home A/B screen.

Pump 3130 may be programmed to generate and display an error message such as "The auto-program received contains a value that exceeds a system limit. Or the values cause a calculated parameter to exceed a system limit." One or more system limits may be hard-coded into pump 3130 and/or included in the drug library. The system limits may pertain to a rate. For example, the pump 3130 may be able to pump at a maximum rate of 999 mL/hr. If an auto-program request is received at a rate greater than 999 mL/hr., for example say 2000 mL/hr., pump 3130 may display the error message. Similar system limits may exist for other information such as duration, VTBI, and the like. Along with the error message, pump 3130 may display the suggested action, e.g., "Press OK now, or wait for this screen to automatically dismiss".

In some instances, pump 3130 may display an error message such as "The auto-program is for a line that contains unconfirmed programming data". This might happen if the caregiver got called away on an emergency to help another patient or co-worker before confirming the programming data. Pump 3130 may also display the corresponding suggested action "Resubmit the auto-program. All unconfirmed data will be cleared." Thus, in response to the error message, caregiver 3132 may either resubmit the auto-program or reject the auto-program. If the user elects to resubmit the auto-program, all of the unconfirmed data previously entered will be cleared and thereafter replaced with the data from the resubmitted auto-program. If the caregiver rejects the auto-program, the unconfirmed data will be maintained and the user is taken to the last input screen used or the home A/B screen.

Pump 3130 may generate an error message at screen 603 stating "The auto-program is rejected because of a partially programmed line." A line is partially programmed when a drug is selected for the line and the line program has not been cleared or confirmed. A pump with an installed cassette was started. The CCA was selected. A new IV bag containing the same or different drug was hung. The user manually selects one of the lines and a medication on the pump. The user then switches part way through the programming sequence to the auto-program process, wherein the barcode on the drug container is scanned and the order sent. The standard auto-program for line A is sent to the infuser, which rejects the auto-program because a manual program was already partially input. On the same screen, the suggested course of action is displayed: "Press [Clear] and resubmit the auto-program. All unconfirmed data will be cleared."

Caregiver 3132 may select a "Standby" input option at pump 3130 for a particular channel. The standby input option is selected to suspend for an indefinite time, up to 72 hours, an infusion that has already been programmed on a particular channel or infusion line. The standby option can be used prior to an infusion being started if the caregiver is unsure of the time the infusion should be started. For example, the caregiver can set up the pump and it can be programmed, but the patient may not yet be present at their bed. However, unlike the delayed start option which inserts a predetermined delay prior to the start of a programmed infusion, the standby option also can be selected during the execution of a programmed infusion. It would be undesirable in most cases for a previously programmed and started infusion program to be automatically supplanted by a new set of infusion pump settings through an auto-programming message or request. Thus, the pump 3130 may not accept an auto-program request for a channel or line that is already in standby mode. When a request is received for a line in standby, pump 3130 may display an error message such as "The auto-program is for a line which is in Standby". Similarly, pump 3130 may not accept an auto-program request for a channel or line that is "Delay Start" mode. As discussed above, "Delay Start" may enable a caregiver 3132 to input auto-program settings to be started automatically at a later time (X number of minutes or hours later), wherein the later time may be predetermined, known and selected by the caregiver 3132. If pump 3130 receives a request for auto-program on a line which is in "Delay Start" mode, pump 3130 may display an error message such as "The auto program is for a line which is in Delay Start". For both the Standby and Delay Start error messages, pump 3130 may display a suggested action, e.g., "Clear this line and resubmit the auto-program". This suggested action may advise the caregiver 3132 to clear the line that is in either "Standby" or "Delay Start" mode and then resubmit the auto-program request.

Pump 3130 may display the error message "The auto-program is for a line that has an active alarm that stops or prevents delivery, thus the auto-program is not valid in this alarm condition." Pump 3130 may be capable of outputting alarms for various situations or conditions. For example, the pump 3130 battery may be almost dead and not plugged in to a power source. In another example, a high priority alarm may be in progress. During these situations, pump 3130 may not accept an auto-program request and, along with the error message, may display the suggested action "Clear the alarm condition and resubmit the auto-program". Clearing the alarm may comprise eliminating the condition causing the alarm (such as replacing or charging the pump battery).

Because of the unique concurrent delivery capabilities of the PLUM™ infusion pump, two different medications can be delivered from two different source containers upstream of the pump, effectively at the same time through a single line to the patient downstream of the pump. The pump can also switch back and forth from delivering medication from lines A and B respectively, and vice versa, making separate but coordinated "piggyback" delivery possible and convenient. However, this can lead to some rather complex scenarios from an auto-programming perspective. Many things can go wrong and lead to errors, including failures, unintended consequences or problems. Previously many of these errors would not have been communicated to the caregiver at the pump or on its display screen. Recall from above that the pump may have a rate limit of 999 mL/hr. The pump may have certain low flow limitations too. Thus, in certain aspects, pump 3130 may display an error message such as "The auto-program is not valid due to concurrency violation. Delivery A+B greater than 500 mL/hr or less than 0.5 mL/hr for each line." Although the pump is physically capable of 999 mL/hr. through a single line, when concurrent delivery is taking place through two lines (A and B) only 500 mL/hr. is permitted for each of the lines A and B. Otherwise, if each line were to be programmed to deliver 500 mL/hr. or more, the pump system rate limit of 999 mL/hr. would be exceeded. Also, each line must also be programmed to deliver at least 0.5 mL/hr. or more for proper pump operation. As discussed above, on the same screen, pump 3130 may display the suggested action, e.g., "Press OK now, or wait for this screen to automatically dismiss". For greater clarity to the pump user, the specific cause for the concurrency violation could be specified. For example, the error message could read "Delivery of A+B greater than 500 mL/hr" or "Delivery A+B less than 0.5 mL/hr" depending upon the specific cause. Concurrency errors can result from various situations as well. For example, an auto-program can be rejected for a concurrency violation when a new IV bag or container or rate change is requested for Line A or Line B when B is running in concurrent, which would result in a concurrency violation, i.e., delivery greater than 500 mL/hr. for the sum of the two lines or less than 0.5 mL/hr. on each line. Alternatively a concurrency violation can happen on the first attempt to program an initial concurrent delivery on Line B. The error messages can be tailored to more clearly indicate the specific situation that caused the rejection of the auto-program.

In some aspects, infusion pump 3130 may be configured to pump primary medications through line A and secondary medication through line B in a separate but coordinated piggyback delivery in series. In some cases, an auto-program request for line B may cause an interruption to the pumping medication in line A. This may be undesirable, particularly when the medication pumping in line A is vital such as critical medications including but not limited to Dopamine, Heparin or Insulin. Thus, when the infusion pump 3130 receives an auto-program for line B in step 651, the infusion pump 3130 may at step 653 make a determination whether a medication on that or another line is interruptible. If the answer is affirmative, then the process can continue to screen 605, step 655, etc. If the answer is negative, the pump 3130 can display an error message at screen 603 such as "The auto-program is not valid for line B. The medication delivering for line A cannot be interrupted." Similarly, infusion pump 3130 may display an error message such as "The auto-program is not valid for line A. The medication in the Auto-Program is not interruptible and Line B is delivering a Piggyback infusion." Correspondingly, pump 3130 may display the suggested action "Press OK now, or wait for this screen to automatically dismiss".

Pump 3130 may display the same suggested action on a screen with an error message such as "The auto-program is not valid because the weight of the patient in the Auto-Program does not match the weight of the patient on the program delivering on the other line." The infusion pump 3130 may generate this or similar error message when the weight or expected weight range entered for a patient is inconsistent among the multiple lines. For instance, a nurse may enter a weight of 75 kg for a patient on line A and then a weight of 7.5 kg for the same patient on line B. These inconsistent weights may cause infusion pump 3130 to display the error message. Similarly, pump 3130 may display an error message such as "The auto-program is not valid because the height of the patient in the auto-program does not match the height of the patient on the program delivering on the other line." In this case, pump 3130 may ensure that the height or expected height range of the patient receiving medication is consistent on line A and line B. Similarly, pump 3130 may display an error message such as "The auto-program is not valid because the BSA in the auto-program does not match the BSA on the program delivering on the other line." BSA means body surface area and is usually estimated or calculated based on a patient's body mass and height. BSA is also sometimes expressed as BMI or body mass index and some drugs are dosed on this basis.

As discussed previously, a caregiver 3132 may be required to enter a CCA prior to programming the pump 3130 manually or submitting an auto-program request. If no CCA is received or a CCA not stored in the drug library is received, infusion pump 3130 may display an error message such as "The Auto-Program is not valid because a CCA has not been selected on the infuser." Pump 3130 may also suggest the action, e.g., "Select a CCA and resubmit the Auto-Program".

Pump 3130 may comprise a lock to the keypad shown in FIG. 4. When the keypad is locked, pump 3130 may not receive commands submitted by selecting buttons on the keypad. Pump 3130 also may not receive auto-programming requests when the keypad is locked. In those cases, pump 3130 may display an error message such as "The auto-program is not valid because the keypad is locked." The infusion pump 3130 may also display the suggested action, e.g., "Unlock the keypad." After caregiver 3132 unlocks the keypad, pump 3130 may automatically accept the auto-programming request.

The remaining error messages discussed below may be displayed in conjunction with the suggested action, e.g., "Press OK now, or wait for this screen to automatically dismiss". As discussed above, after selection of the "OK" input option or waiting for the screen to automatically dismiss after the timeout period, pump 3130 may display the home A/B screen.

Pump 3130 may, in some cases, generate and display an error message such as "The Auto-Program is not valid because the received parameters will not result in a valid dose." When two out of the three parameters or variables volume, (flow) rate and duration are provided to the pump 3130, its processor can calculate a dose. Normally when a certain dosage is being targeted or ordered by the doctor, it is based upon the weight of the patient. The drug may be available as an amount or mass in a given volume of diluent such as 5 mg/1000 mL IV container. When there is no combination of values of flow rate and duration that will result in a valid dose, this error message is generated.

Infusion pump 3130 may display an error message such as "The auto-program is not valid because the Rate cannot be titrated when VTBI is 0." This error message may be displayed when a caregiver 3132 enters a rate for a medication to be pumped while also entering a total volume of the medication to be infused of 0 mL. Pump 3130 may therefore require a VTBI greater than 0. The auto-program might be a change to a currently running program—a "titration." However, if there is no VTBI left to infuse in the program, the rate or other parameters cannot effectively be changed because there is no volume left to be infused. Similarly, infusion pump 3130 may display an error message such as "The auto-program is not valid because it is a titration for a line that has no confirmed program." A titration is by definition a change in rate, duration or VTBI in a currently running or already programmed infusion. Thus, you cannot auto-program a titration or change for a line or pump channel until after it has a prior program that has been confirmed.

In certain aspects, pump 3130 may display an error message such as "The auto-program is not valid for a line with a Multistep or Loading dose program." If the line is busy with a multistep infusion or loading dose program, that program must be completed or cleared before any new auto-program request can be received and executed.

Infusion pump 3130 may display an error message such as "The Auto-Program was rejected by Hospira MedNet due to incomplete or corrupt data." This might be highlighted by a checksum failure or handshake failure. Part of the auto-program message may have been lost or corrupted for one reason or another.

Pump 3130 may display an error message such as "The Auto-Program for this infuser was rejected by Hospira MedNet™ due to drug library incompatibility." The drug library identified in the device manifest for the auto-program message is not recognized. In other words, the active drug library mentioned in the auto-program manifest does not match what the MMU server 3108 and/or the pump itself thinks is the appropriate drug library that is in the pump. For example, the drug library has an identifier (perhaps an alphanumerical string) that may include the pump type and version of the drug library. For some reason, the drug library version may get out of synch between the infusion pump and the MMU such that drug library identifier in the auto-program request does match the drug library that is currently in the infusion pump.

FIG. 7 illustrates a flow chart of a process 700 in accordance with aspects of the disclosure. Process 700 may be carried out using infusion pump 3130 shown in FIG. 4. Step 701 may comprise receiving an auto-programming request, wherein the auto-programming request may comprise IV bag or drug container information such as drug name, concentration or other drug identifying information, and infusion pump information, and optionally patient identification information. Step 703 may comprise receiving infusion program settings, parameters or variables including but not limited to dose, flow rate, duration and volume. Step 705 may comprise comparing the infusion program settings with drug library program settings, wherein the drug library program settings are included in rule sets that place soft (breachable) limits and hard (non-breachable) limits provided in a drug library stored at the infusion pump. Step 707 may comprise determining whether the infusion program settings are consistent or inconsistent with the drug library program settings based on the comparing.

Step 709 may comprise generating an error message based on the determining that the infusion program settings are inconsistent with the drug library settings. Step 711 may comprise displaying a screen, wherein the screen comprises the error message and a suggested action. In some aspects, other steps may be performed as discussed above in connection with FIGS. 1-6.

In at least one embodiment of the invention, if the infusion program settings are consistent with the drug library program settings based on the comparing, at step 713 the at least one infusion pump 3130 compares the at least one stale auto-program received to the at least one completed or running manual infusion program based on an approximate time of infusion administration and parameter matching logic including infusion administration parameters and infusion pump operating parameters, to determine if the at least one previously completed or running manual infusion program is acceptable based on the potential matches as discussed previously.

At step 715, in one or more embodiments, the at least one infusion pump 3130 saves the acceptably completed or running manual infusion programs for later analysis. In at least one embodiment, at step 715, the at least one infusion pump may optionally notify the at least one caregiver 3132 of the acceptable at least one completed or running manual infusion program instead of the at least one auto-program as the acceptable program.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. For example, the first computer can be in the HIS/POC or other computer system inside or outside the healthcare facility such that the MMU 3108 is not required to communicate with the infusion pump 3130. Therefore, it is the intent to cover all such modifications and alternate embodiments as may come within the true scope of this invention.

What is claimed is:

1. A infusion pump configured to communicate with a first computer using a computer network interface, the infusion pump configured to:
    receive a manual infusion program comprising first infusion program settings,
    execute said manual infusion program,
    receive a stale auto-program comprising second infusion program settings, wherein the stale auto-program was previously unable to be transmitted to the infusion pump,
    determine differences between said first infusion program settings of said manual infusion program and said second infusion program settings of said stale auto-program are within a predefined tolerance, and
    save said manual infusion program as an acceptable manual infusion program.

2. The infusion pump of claim 1, wherein said manual infusion program is provided in a drug library stored at said infusion pump.

3. The infusion pump of claim 1, wherein said infusion pump is further configured to save said differences between said first infusion program settings of said manual infusion program and said second infusion program settings of said stale auto-program to a remote server.

4. The infusion pump of claim 1, wherein said infusion pump is further configured to receive said manual infusion program from a caregiver and save identification data associated with said caregiver.

5. The infusion pump of claim 1, wherein said infusion pump is further configured to determine a scoring of accuracy based on said differences between said first infusion program settings of said manual infusion program and said second infusion program settings of said stale auto-program, wherein said scoring of accuracy comprises an acceptability level of said manual infusion program.

6. The infusion pump of claim 1, wherein said infusion pump is further configured to generate a report from said differences between said first infusion program settings of said manual infusion program and said second infusion program settings of stale auto-program, and wherein said report comprises one or more of a time differential between a completion time of said manual infusion program and a completion time of said stale auto-program, a scoring of accuracy comprising an acceptability level of said manual infusion program and said stale auto-program, and a rating of a caregiver.

7. The infusion pump of claim 1, wherein said infusion pump is further configured to transmit said manual infusion program to said first computer, and wherein said first computer is further configured to save said manual infusion program and identification data of a caregiver.

8. The infusion pump of claim 1, wherein said infusion pump is further configured to compare said first infusion program settings of said manual infusion program to said second infusion program settings of said stale auto-program to determine a scoring of accuracy comprising an acceptability level of said manual infusion program.

9. The infusion pump of claim 1, wherein said infusion pump is further configured to generate a report from said differences between said first infusion program settings of said manual infusion program and said second infusion program settings of said stale auto-program, wherein said report comprises one or more of a time differential between completion time of said manual infusion program and a completion time of said stale auto-program, a scoring of accuracy comprising an acceptability level of said manual infusion program, and a rating of a caregiver.

10. The infusion pump of claim 1, wherein said infusion pump is further configured to verify the infusion program settings against a drug library installed on the infusion pump.

11. The infusion pump of claim 1, wherein said stale auto-program further comprises fluid container information and infusion pump information.

12. The infusion pump of claim 1, wherein the first infusion program settings or the second infusion program settings comprises infusion pump operating parameters, a volume to be infused, or a rate of delivery.

13. A method for identifying an acceptable manual infusion program at an infusion pump comprising:
    receiving a manual infusion program,
    executing said manual infusion program,
    receiving a stale auto-program from a first computer,
    comparing one or more infusion parameters of said stale auto-program to corresponding one or more infusion parameters of said manual infusion program,
    determining, based on the comparing, that differences between the stale auto-program and the manual infusion program are within a predefined tolerance, and saving said manual infusion program as the acceptable manual infusion program.

14. The method of claim 13, further comprising saving said manual infusion program in a drug library stored at said infusion pump.

15. The method of claim 13, further comprising saving said differences to a remote server.

16. The method of claim 13, further comprising verifying the infusion program settings against a drug library installed on the infusion pump.

17. The method of claim 13, further comprising:
receiving, via said first computer, an infusion auto-program from a remote source, wherein said infusion auto-program comprises infusion program settings; and
queuing said infusion auto-program when said first computer is unable to transmit said infusion auto-program to said at least one infusion pump, wherein said queued infusion auto-program becomes the stale auto-program.

18. The method of claim 13, further comprising saving a first event alert indicating the manual infusion program as an acceptable potential match.

19. The method of claim 13, further comprising saving a second event alert indicating the auto-program as an un-executed program if the manual infusion program is an acceptable potential match.

20. The method of claim 13, wherein said stale infusion auto-program comprises IV drug container information, infusion pump information, and infusion program settings.

* * * * *